United States Patent
Mahmood et al.

(10) Patent No.: US 12,285,502 B2
(45) Date of Patent: Apr. 29, 2025

(54) HER3 PEPTIDES FOR IMAGING AND RADIOTHERAPY

(71) Applicant: The General Hospital Corporation, Boston, MA (US)

(72) Inventors: Umar Mahmood, Winchester, MA (US); Benjamin Larimer, Woburn, MA (US)

(73) Assignee: The General Hospital Corporation, Boston, MA (US)

(\*) Notice: Subject to any disclaimer, the term of this patent is extended or adjusted under 35 U.S.C. 154(b) by 434 days.

(21) Appl. No.: 17/562,861

(22) Filed: Dec. 27, 2021

(65) Prior Publication Data

US 2022/0175975 A1 Jun. 9, 2022

Related U.S. Application Data

(62) Division of application No. 16/475,020, filed as application No. PCT/US2017/069031 on Dec. 29, 2017, now Pat. No. 11,241,511.

(60) Provisional application No. 62/440,052, filed on Dec. 29, 2016.

(51) Int. Cl.
| | |
|---|---|
| *A61K 38/10* | (2006.01) |
| *A61K 51/08* | (2006.01) |
| *A61P 31/00* | (2006.01) |
| *C07K 7/08* | (2006.01) |

(52) U.S. Cl.
CPC ............ *A61K 51/088* (2013.01); *A61K 38/10* (2013.01); *A61P 31/00* (2018.01); *C07K 7/08* (2013.01)

(58) Field of Classification Search
CPC . A61K 5/00; A61K 5/08; A61K 5/088; A61K 38/08; A61K 38/12; A61K 51/088; A61P 31/00; C07K 7/08; C07K 7/64
USPC .......... 424/1.11, 1.49, 1.65, 1.69, 1.81, 1.85, 424/1.89, 9.1, 9.2, 9.3, 9.4, 9.5, 9.6; 514/1, 1.1, 19.2, 19.3, 19.4, 19.5, 19.6, 514/21.1, 21.5, 21.9; 530/300, 317, 321, 530/328, 330; 534/7, 10–16
See application file for complete search history.

(56) References Cited

U.S. PATENT DOCUMENTS

| | | | |
|---|---|---|---|
| 4,472,509 | A | 9/1984 | Gansow et al. |
| 4,938,948 | A | 7/1990 | Ring et al. |
| 5,021,236 | A | 6/1991 | Gries et al. |
| 5,889,155 | A | 3/1999 | Ashkenazi et al. |
| 11,241,511 | B2 * | 2/2022 | Mahmood ............... A61P 31/00 |
| 11,559,590 | B2 * | 1/2023 | Mahmood ............... A61B 5/00 |
| 2013/0137774 | A1 | 5/2013 | Greene et al. |
| 2015/0252079 | A1 | 9/2015 | Malm et al. |
| 2015/0265733 | A1 | 9/2015 | Maecke et al. |

FOREIGN PATENT DOCUMENTS

WO    WO-2018126183 A2 *   7/2018 ........... A61K 51/088

OTHER PUBLICATIONS

Bosch et al., "PI3K inhibition results in enhanced estrogen receptor function and dependence in hormone receptor-positive breast cancer," Science Translational Medicine, Apr. 2015, 7(283):283ra51-283ra51.
Da Pieve et al., "Efficient [18F]AIF Radiolabeling of ZHER3:8698 Affibody Molecule for Imaging of HER3 Positive Tumors," Bioconjugate Chemistry, Jun. 2016, 27(8):1839-1849.
Ferguson et al., "Extracellular domains drive homo-but not heterodimerization of erbB receptors," EMBO J., Sep. 2000, 19(17):4632-4643.
García et al., "Dual mTORC1/2 and HER2 blockade results in antitumor activity in preclinical models of breast cancer resistant to anti-HER2 therapy," Clinical Cancer Research, May 2012, 18(9):2603-2612.
Gardner et al., "Interaction of peptides related to secretin with hormone receptors on pancreatic acinar cells," Gastroenterology, Dec. 1976, 71(6):965-970.
Herbst et al., "TRIBUTE: A phase III trial of erlotinib hydrochloride (OSI-774) combined with carboplatin and paclitaxel chemotherapy in advanced non-small-cell lung cancer," Journal of Clinical Oncology, Sep. 2005, 23(25):5892-5899.
Houghten, "General method for the rapid solid-phase synthesis of large numbers of peptides: specificity of antigen-antibody interaction at the level of individual amino acids," Proceedings of the National Academy of Sciences, Aug. 1985, 82(15):5131-5135.
Larimer and Deutscher, "Development of a peptide by phage display for SPECT imaging of resistance-susceptible breast cancer," American Journal of Nuclear Medicine and Molecular Imaging, Aug. 2014, 4(5):435-447.
Larimer et al. "Phage Display Selection, In Vitro Characterization, and Correlative PET Imaging of a Novel HER3 Peptide," Molecular Imaging and Biology, Apr. 2018, 20(2):300-308.
Larimer et al., jnm.snmjournals.org [online], "Phage display selection of a novel HER3 Pet imaging peptide for targeted therapy resistance prediction," May 1, 2017, retrieved on Feb. 21, 2020, retrieved from URL<http://jnm.snmjournals.org/content/58/supplement_1/690>, 2 pages.
Larimer, "Quantitative PET Imaging with Novel HER3-Targeted Peptides Selected by Phage Display to Predict Androgen-Independent Prostate Cancer Progression," Technical Report, Defense Technical Information Center, 2017, 20 pages.

(Continued)

*Primary Examiner* — Jeffrey E. Russel
(74) *Attorney, Agent, or Firm* — Fish & Richardson P.C.

(57) ABSTRACT

Provided herein are compositions of Formula I useful for imaging HER3. The structure of Formula I is A-B-C, where A is an imaging agent, B is a linking group or a covalent bond, and C is a polypeptide comprising from about 9 to about 75 amino acids and contains a disulfide bond between two cysteine groups. An exemplary composition provided herein is useful as a radiotracer for position emission tomography (PET) imaging. Methods of imaging HER3 and combination therapies comprising the HER3 imaging agents are also provided.

12 Claims, 8 Drawing Sheets
Specification includes a Sequence Listing.

(56) References Cited

OTHER PUBLICATIONS

Merrifield et al., "Solid phase peptide synthesis. I. The synthesis of a tetrapeptide," Journal of the American Chemical Society, Jul. 1963, 85(14) 2149-2154.

O'Brien et al., "Predictive biomarkers of sensitivity to the phosphatidylinositol 3' kinase inhibitor GDC-0941 in breast cancer preclinical models," Clin. Cancer. Res., Jul. 2010, 16(14):3670-3683.

Orlova et al., "Imaging of HER3-expressing xenografts in mice using a (99m)Tc(CO) 3-HEHEHE-Z HER3 08699 affibody molecule," European Journal of Nuclear Medicine and Molecular Imaging, Mar. 2014, 41(7):1450-1459.

PCT International Preliminary Report on Patentability in International Appln. No. PCT/US2017/069031, dated Jul. 2, 2019, 8 pages.

PCT International Search Report and Written Opinion in International Appln. No. PCT/US2017/069031, dated Jul. 16, 2018, 13 pages.

Schlessinger, "Cell signaling by receptor tyrosine kinases," J. Cell, Oct. 2000, 103(2):211-225.

Sergina et al., "Escape from HER-family tyrosine kinase inhibitor therapy by the kinase-inactive HER3," Nature, Jan. 2007, 445(7126):437-441.

Shi et al., "ErbB3/HER3 intracellular domain is competent to bind ATP and catalyze autophosphorylation," Proceedings of the National Academy of Sciences, Apr. 2010, 107(17):7692-7697.

Slamon et al., "Use of chemotherapy plus a monoclonal antibody against HER2 for metastatic breast cancer that overexpresses HER2," New England Journal of Medicine, Mar. 2001, 344(11):783-792.

Tao et al., "Antagonism of EGFR and HER3 enhances the response to inhibitors of the PI3K-Akt pathway in triple-negative breast cancer," Science Signaling, Mar. 2014, 7(318):ra29.

Wang et al., "Different mechanisms for resistance to trastuzumab versus lapatinib in HER2-positive breast cancers-role of estrogen receptor and HER2 reactivation," Breast Cancer Res., Dec. 2011, 13(6):R121.

Wehrenberg-Klee et al., "Differential receptor tyrosine kinase PET imaging for therapeutic guidance," Journal of Nuclear Medicine, Sep. 2016, 57(9):1413-1419.

Yarden & Sliwkowski, "Untangling the ErbB signalling network," Nature Reviews Molecular Cell Biology, Feb. 2001, 2(2):127-137.

* cited by examiner

5A
| Organ | %ID/g |
|---|---|
| Tumor | 0.50±0.18 |
| Blood | 0.18±0.04 |
| Heart | 0.31±0.07 |
| Lungs | 0.70±0.14 |
| Stomach | 0.30±0.07 |
| Intestines | 0.48±0.15 |
| Liver | 0.70±0.23 |
| Kidney | 10.1±1.67 |
| Spleen | 0.38±0.09 |
| Muscle | 0.28±0.14 |
| Bone | 0.67±0.38 |
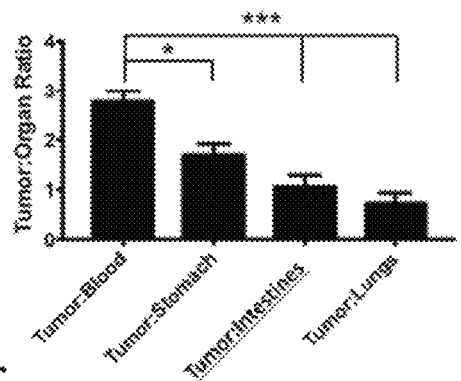
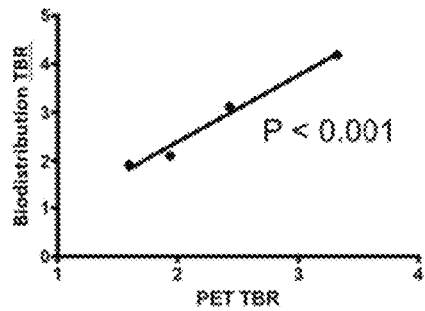
Figures 5A-5C

HER3 PEPTIDES FOR IMAGING AND RADIOTHERAPY

CROSS-REFERENCE TO RELATED APPLICATIONS

This application is a divisional of U.S. patent application Ser. No. 16/475,020, filed on Jun. 28, 2019, which is the U.S. National Stage of PCT International Patent Application No. PCT/US2017/069031, filed on Dec. 29, 2017, which claims the benefit of U.S. Provisional Application Ser. No. 62/440,052, filed Dec. 29, 2016, the disclosure of which is incorporated herein by reference in its entirety.

FEDERALLY SPONSORED RESEARCH OR DEVELOPMENT

This invention was made with Government support under Grant No. W81XWH-16-1-0447, awarded by the Department of Defense. The Government has certain rights in the invention.

SEQUENCE LISTING

This application contains a Sequence Listing that has been submitted electronically as an ASCII text file named "29539-0258002_ST25.txt." The ASCII text file, created on Sep. 18, 2024, is 12,489 kilobytes in size. The material in the ASCII text file is hereby incorporated by reference in its entirety.

TECHNICAL FIELD

This invention relates to compositions useful for imaging techniques, and more particularly to compounds that are useful for imaging HER3 using medical imaging, including positron emission tomography.

BACKGROUND

The receptor tyrosine kinase HER3 (ERBB3) is upregulated in response to targeted therapies in multiple cancers, including lung, breast and prostate cancers. Levels of HER3 expression are highly dynamic, making quantification by tissue sampling techniques such as biopsy potentially inaccurate. PET imaging, which permits global and serial imaging, may present a more robust method for HER3 quantification, improving HER3 diagnosis, facilitating improved clinical trials assessing HER3 expression, and, in the long term, providing accurate diagnosis of HER3 status to help diagnosis targeted therapy resistance.

SUMMARY

The present application provides, inter alia, a composition of Formula I:

A-B-C    I wherein:
A comprises an imaging agent;
B is a linking group or a covalent bond; and
C is a polypeptide comprising from about 9 to about 75 amino acids, wherein the polypeptide comprises an amino acid sequence having at least 90% sequence identity to:

(SEQ ID NO: 12)

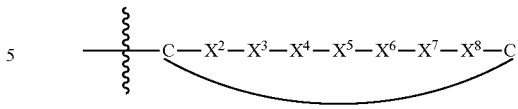

wherein:
〰️ refers to the bond between C and B;

refers to a disulfide bond between the cysteine groups;
$X^2$ is selected from the group consisting of L, L*, I, I*, P, P*, V, V*, G, and G*;
$X^3$ is selected from the group consisting of P, P*, L, L*, I, I*, V, V*, G, and G*;
$X^4$ is selected from the group consisting of T, T*, S, S*, C, C*, M, and M*;
$X^5$ is selected from the group consisting of any L-amino acid, any D-amino acid, and any non-natural amino acid;
$X^6$ is selected from the group consisting of any L-amino acid, any D-amino acid, and any non-natural amino acid;
$X^7$ is selected from the group consisting of R, R*, H, H*, K, K*, N, N*, Q, and Q*, and
$X^8$ is selected from the group consisting of S, S*, T, T*, C, C*, M, and M*,
wherein:
L* is a non-natural derivative of L;
I* is a non-natural derivative of I;
P* is a non-natural derivative of P;
V* is a non-natural derivative of V;
G* is a non-natural derivative of G;
T* is a non-natural derivative of T;
S* is a non-natural derivative of S;
C* is a non-natural derivative of C;
M* is a non-natural derivative of M;
R* is a non-natural derivative of R;
H* is a non-natural derivative of H;
K* is a non-natural derivative of K;
N* is a non-natural derivative of N; and
Q* is a non-natural derivative of Q.

In some embodiments, A comprises one or more imaging agents selected from the group consisting of a paramagnetic ion, an x-ray imaging agent, a fluorophore, and a radioisotope. In some embodiments, A comprises a radioisotope. In some embodiments, the radioisotope is suitable for PET imaging. In some embodiments, the radioisotope is selected from the group consisting of $^{3}$H, $^{11}$C, $^{14}$C, $^{18}$F, $^{32}$P, $^{35}$S, $^{36}$Cl, $^{51}$Cr, $^{52}$Fe, $^{57}$Co, $^{58}$Co, $^{59}$Fe, $^{64}$Cu, $^{67}$Cu, $^{67}$Ga, $^{68}$Ga, $^{75}$Se, $^{76}$Br, $^{77}$Br, $^{89}$Zr, $^{90}$Y, $^{99m}$Tc, $^{111}$In, $^{123}$I, $^{124}$I, $^{125}$I, $^{131}$I, $^{152}$Eu, $^{153}$Sm, $^{166}$Ho, $^{177}$Lu, $^{186}$Re, $^{188}$Re, $^{201}$Tl, $^{203}$Pb, $^{210}$At, $^{211}$At, $^{212}$Bi, $^{213}$Bi, and $^{225}$Ac. In some embodiments, the radioisotope selected from the group consisting of $^{3}$H, $^{11}$C, $^{14}$C, $^{18}$F, $^{35}$S, $^{52}$Fe, $^{58}$Co, $^{64}$Cu, $^{68}$Ga, $^{76}$Br, $^{77}$Br, $^{89}$Zr, $^{111}$In, $^{123}$I, $^{124}$I, $^{125}$I, $^{131}$I, $^{186}$Re, $^{188}$Re, and $^{201}$Tl. In some embodiments, A comprises $^{68}$Ga.

In some embodiments, A further comprises a chelating agent. In some embodiments, the chelating agent is selected from the group consisting of 1,4,7-triazacyclononanetriacetic acid (NOTA), 1,4,7,10-tetraazacyclododecane-1,4,7, 10-tetraacetic acid (DOTA), 1,4,7-triazacyclononane-1-glutaric acid-4,7-diacetic acid (NODAGA), ethylene diamine tetra-acetic acid (EDTA), diethylene triaminepentaacetic acid (DTPA), cyclohexyl-1,2-diaminetetraacetic acid (CDTA), ethyleneglycol-O,O'-bis(2-aminoethyl)-N,N,N',N'-tetraacetic acid (EGTA), N,N-bis(hydroxybenzyl)-ethylenediamine-N,N'-diacetic acid (HBED), triethylene tetramine hexaacetic acid (TTHA), hydroxyethylethylenediaminetriacetic acid (HEDTA), 1,4,8,11-tetraazacyclotetradecane-N,N',N'',N'''-tetraacetic acid (TETA), 1,4,7,10-tetraaza-1,4,7,10-tetra-(2-carbamoyl methyl)-cyclododecane (TCMC), and 2,2',2''-(2-(4-isothiocyanatobenzyl)-1,4,7-triazonane-1,4,7-triyl)triacetic acid (NOTA-NCS). In some embodiments, the chelating agent is selected from the group consisting of 1,4,7-triazacyclononanetriacetic acid (NOTA), 1,4,7,10-tetraazacyclododecane-1,4,7,10-tetraacetic acid (DOTA), 1,4,7-triazacyclononane-1-glutaric acid-4,7-diacetic acid (NODAGA), and 2,2',2''-(2-(4-isothiocyanatobenzyl)-1,4,7-triazonane-1,4,7-triyl)triacetic acid (NOTA-NCS). In some embodiments, the chelating agent is 1,4,7-triazacyclononanetriacetic acid (NOTA) or 2,2',2''-(2-(4-isothiocyanatobenzyl)-1,4,7-triazonane-1,4,7-triyl)triacetic acid (NOTA-NCS). In some embodiments, B is a linking group.

In some embodiments, B is a linking group comprising one or more $C_{1-30}$ alkyleneoxy groups, one or more independently selected amino acids, or any combination thereof. In some embodiments, B is a linking group comprising from about 1 to about 10 independently selected amino acids. In some embodiments, B is a linking group comprising a sequence having at least 90% sequence identity to:

(SEQ ID NO: 2)

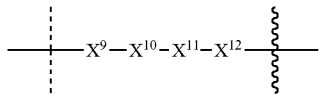

wherein:
------ refers to the bond between B and A;
∿∿∿ refers to the bond between B and C;
$X^9$ is selected from the group consisting of beta A, 6-aminohexnoic acid, 8-aminooctanoic acid, and 2-(2-(2-aminoethoxy) ethoxy) acetic acid;
$X^{10}$ is selected from the group consisting of G, G*, A, A*, S, S*, P, P*, W, W*, Y, Y*, H, H*, T, T*, M, M*, N, N*, Q, and Q*;
$X^{11}$ is selected from the group consisting of G, G*, A, A*, S, S*, P, P*, W, W*, Y, Y*, H, H*, T, T*, M, M*, N, N*, Q, and Q*; and
$X^{12}$ is selected from the group consisting of G, G*, A, A*, S, S*, P, P*, W, W*, Y, Y*, H, H*, T, T*, M, M*, N, N*, Q, and Q*;
wherein:
G* is a non-natural derivative of G;
A* is a non-natural derivative of A;
S* is a non-natural derivative of S;
P* is a non-natural derivative of P;
W* is a non-natural derivative of W;
Y* is a non-natural derivative of Y;
H* is a non-natural derivative of H;
T* is a non-natural derivative of T;
M* is a non-natural derivative of M;
N* is a non-natural derivative of N; and
Q* is a non-natural derivative of Q.

In some embodiments, B is a linking group which is:

(SEQ ID NO: 3)

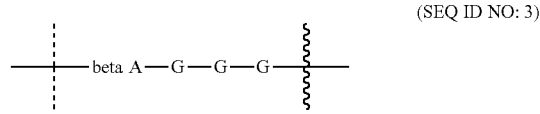

wherein:
------ refers to the bond between B and A; and
∿∿∿ refers to the bond between B and C.

In some embodiments, C is a polypeptide comprising from about 15 to about 25 amino acids, wherein the polypeptide comprises an amino acid sequence having at least 90% sequence identity to SEQ ID NO: 12.

In some embodiments, $X^2$ is L or L*.
In some embodiments, $X^3$ is P or P*.
In some embodiments, $X^4$ is T or T*.
In some embodiments, $X^5$ is K or K*.
In some embodiments, $X^6$ is F or F*.
In some embodiments, $X^7$ is R or R*.
In some embodiments, $X^8$ is S or S*.

In some embodiments, the composition of Formula I is a composition of Formula Ia:

(SEQ ID NO: 4)

Ia

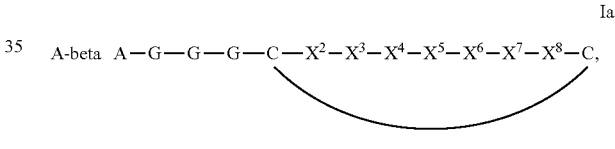

wherein

refers to a disulfide bond between the cysteine groups.

In some embodiments, the composition of Formula I is a composition of Formula Ib:

(SEQ ID NO: 5)

Ib

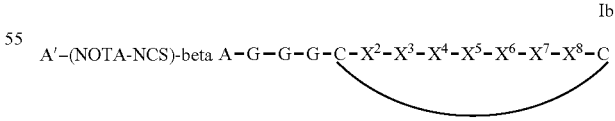

wherein A' is a radioisotope; and

refers to a disulfide bond between the cysteine groups.

In some embodiments, the composition of Formula I is a composition of Formula Ic:

(SEQ ID NO: 5)

Ic

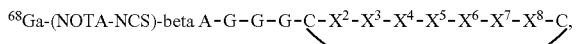
$^{68}$Ga-(NOTA-NCS)-beta A-G-G-G-C-X$^2$-X$^3$-X$^4$-X$^5$-X$^6$-X$^7$-X$^8$-C, wherein

refers to a disulfide bond between the cysteine groups.

In some embodiments, the composition of Formula I is:

(SEQ ID NO: 7)

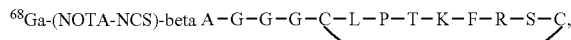
$^{68}$Ga-(NOTA-NCS)-beta A-G-G-G-C-L-P-T-K-F-R-S-C, wherein

refers to a disulfide bond between the cysteine groups.

The present application further provides a composition of Formula II:

B-C

B comprises from about 1 to about 10 amino acids; and
C is a polypeptide comprising from about 9 to about 75 amino acids, wherein the polypeptide comprises an amino acid sequence having at least 90% sequence identity to:

(SEQ ID NO: 12)

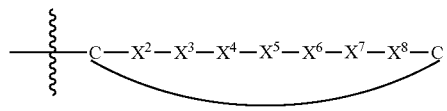
—C—X$^2$—X$^3$—X$^4$—X$^5$—X$^6$—X$^7$—X$^8$—C wherein:
 refers to the bond between C and B;
refers to a disulfide bond between the cysteine groups;
X$^2$ is selected from the group consisting of L, L*, I, I*, P, P*, V, V*, G, and G*;
X$^3$ is selected from the group consisting of P, P*, L, L*, I, I*, V, V*, G, and G*;
X$^4$ is selected from the group consisting of T, T*, S, S*, C, C*, M, and M*;

X$^5$ is selected from the group consisting of any L-amino acid, any D-amino acid, and any non-natural amino acid;
X$^6$ is selected from the group consisting of any L-amino acid, any D-amino acid, and any non-natural amino acid;
X$^7$ is selected from the group consisting of R, R*, H, H*, K, K*, N, N*, Q, and Q*, and
X$^8$ is selected from the group consisting of S, S*, T, T*, C, C*, M, and M*,
wherein:
L* is a non-natural derivative of L;
I* is a non-natural derivative of I;
P* is a non-natural derivative of P;
V* is a non-natural derivative of V;
G* is a non-natural derivative of G;
T* is a non-natural derivative of T;
S* is a non-natural derivative of S;
C* is a non-natural derivative of C;
M* is a non-natural derivative of M;
R* is a non-natural derivative of R;
H* is a non-natural derivative of H;
K* is a non-natural derivative of K;
N* is a non-natural derivative of N; and
Q* is a non-natural derivative of Q.

In some embodiments, B comprises a sequence having at least 90% sequence identity to:

(SEQ ID NO: 8)

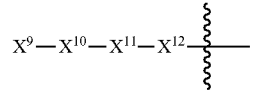
X$^9$—X$^{10}$—X$^{11}$—X$^{12}$— wherein:
refers to the bond between B and C;
X$^9$ is selected from the group consisting of beta A, 6-aminohexnoic acid, 8-aminooctanoic acid, and 2-(2-(2-aminoethoxy) ethoxy) acetic acid;
X$^{10}$ is selected from the group consisting of G, G*, A, A*, S, S*, P, P*, W, W*, Y, Y*, H, H*, T, T*, M, M, N, N*, Q, and Q*;
X$^{11}$ is selected from the group consisting of G, G*, A, A*, S, S*, P, P*, W, W*, Y, Y*, H, H*, T, T*, M, M*, N, N*, Q, and Q*; and
X$^{12}$ is selected from the group consisting of G, G*, A, A*, S, S*, P, P*, W, W*, Y, Y*, H, H*, T, T*, M, M*, N, N*, Q, and Q*;
wherein:
G* is a non-natural derivative of G;
A* is a non-natural derivative of A;
S* is a non-natural derivative of S;
P* is a non-natural derivative of P;
W* is a non-natural derivative of W;
Y* is a non-natural derivative of Y;
H* is a non-natural derivative of H;
T* is a non-natural derivative of T;
M* is a non-natural derivative of M;
N* is a non-natural derivative of N; and
Q* is a non-natural derivative of Q.

In some embodiments, B is:

(SEQ ID NO: 9)

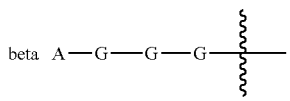

wherein ∿∿∿ refers to the bond between B and C

In some embodiments, C is a polypeptide comprising from about 15 to about 25 amino acids, wherein the polypeptide comprises an amino acid sequence having at least 90% sequence identity to SEQ ID NO: 1.

In some embodiments, $X^2$ is L or L*.
In some embodiments, $X^3$ is P or P*.
In some embodiments, $X^4$ is T or T*.
In some embodiments, $X^5$ is K or K*.
In some embodiments, $X^6$ is F or F*.
In some embodiments, $X^7$ is R or R*.
In some embodiments, $X^8$ is S or S*.

In some embodiments, the composition of Formula II is a composition of Formula IIa:

(SEQ ID NO: 10)

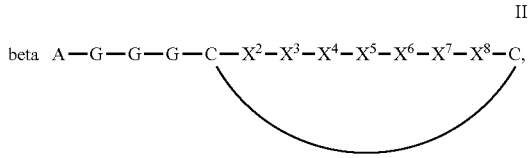

wherein

refers to a disulfide bond between the cysteine groups, wherein

In some embodiments, the composition of Formula II is (SEQ ID NO: 11)

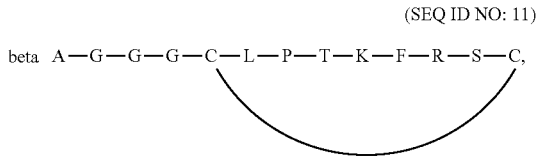

wherein

refers to a disulfide bond between the cysteine groups.

In some embodiments, C is a polypeptide that binds HER3.

The present application further provides a pharmaceutical composition comprising a composition provided herein, and a pharmaceutically acceptable carrier.

The present application further provides a method of imaging cancer in a subject, the method comprising:
i) administering to the subject an effective amount of a composition provided herein (e.g., a composition of Formula I); and
ii) imaging the subject with a suitable imaging technique.

The present application further provides a method of treating a cancer in a subject, the method comprising:
i) administering to the subject an effective amount of a composition provided herein (e.g., a composition of Formula I);
ii) imaging the subject with a suitable imaging technique; and
iii) administering to the subject a therapeutically effective amount of one or more therapeutic agents.

The present application further provides a method of monitoring treatment of a cancer in a subject, the method comprising:
i) administering to the subject an effective amount of a composition provided herein (e.g., a composition of Formula I);
ii) imaging the subject with a suitable imaging technique; and
iii) administering to the subject a therapeutically effective amount of one or more therapeutic agents.

In some embodiments, the methods provided herein further comprise administering an additional effective amount of the composition to the subject after step iii). In some embodiments, the methods provided herein further comprise imaging the subject with a suitable imaging technique after step iii).

In some embodiments, the therapeutic agent is a chemotherapeutic agent. In some embodiments, the therapeutic agent is a HER3 inhibitor. In some embodiments, the therapeutic agent is selected from the group consisting of patritumab, MM-121, U3-1402, GSK2849330, neratinib, lumretuzumab, U3-1287, Sym013, AV-203, trastuzumab, pertuzumab, cetrorelix, enzalutamide, and erlotinib.

In some embodiments, the cancer is a solid tumor. In some embodiments, the cancer is selected from the group consisting of breast cancer, lung cancer, prostate cancer, gastric cancer, head and neck cancer, and ovarian cancer. In some embodiments, the prostate cancer is castration resistant prostate cancer.

In some embodiments, the imaging technique is selected from the group consisting of magnetic resonance (MR) imaging, positron emission tomography (PET) imaging, fluorescent imaging, single photon emission computed tomography (SPECT), luminescent imaging, or any combination thereof. In some embodiments, the imaging technique is positron emission tomography (PET) imaging.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIG. 5A shows biodistribution of $^{68}$Ga-(NOTA-NCS)-HER3P1 in depicted organs as the mean injected dose per gram of tissue (% ID/g) of four 22RV1 tumor bearing mice±SD.

FIG. 5B shows tumor to organ ratios calculated by biodistribution values from FIG. 5A demonstrating specific accumulation in murine sites of non-tumor tissue HER3 expression.

FIG. 5C shows linear regression of TBR from both biodistribution versus PET imaging. Significance of linearity determined by Pearson's correlation. *P<0.05, ***P<0.001.

DETAILED DESCRIPTION

Figures 1A, 1B, 1C:
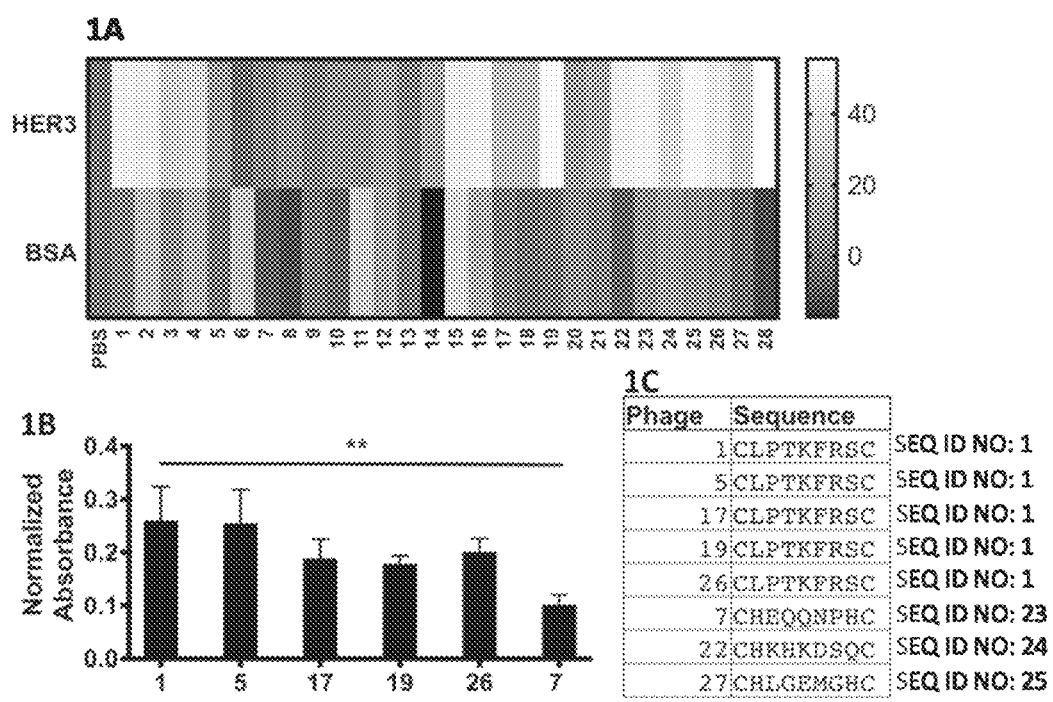
FIG. 1A shows a heat map of standardized phage supernatant binding to HER3 and BSA as a control. White indicates high binding and black indicates low binding.
FIG. 1B shows normalized binding of the 5 highest phage from supernatant phage ELISA, bars represent the mean of 6 replicates ±SEM.
FIG. 1C shows sequences of phages of (SEQ ID NO:1, 23-25) with high binding (1, 5, 17, 19, 26) and low binding (7, 22, 27) to HER3. **P<0.01.

Molecular targeted cancer therapy, while providing benefits for a number of indications, has so far failed to produce durable responses in a majority of patients (see e.g., Herbst et al, *Journal of Clinical Oncology*, 2005, 23:5892-5899). While no single mechanism is entirely responsible for targeted therapy resistance, a recurring theme is the upregulation of feedback loops that circumvent blockade of an oncogenic signaling pathway. Feedback loop signaling can be accomplished through alternative activation of a homologous pathway or through over-expression of a secondary oncogenic protein. One such protein, human epidermal growth factor receptor 3 (HER3), has been implicated in targeted therapy resistance in a number of malignancies including breast, lung and prostate cancer.

HER3 is a member of the epidermal growth factor (EGF) family of receptors that includes EGFR, HER2/ErbB2/neu, HER3/ErbB3 and HER4/ErbB4. The EGFR family canonically function through ligand binding followed by dimerization, phosphorylation and downstream signaling through the MAPK and PI3K/AKT pathways (see e.g., Yarden, Y. *Nature Reviews Molecular Cell Biology*, 2001, 2:127; Schlessinger, J. *Cell*, 2000, 103:211-225; and Ferguson et al, *EMBO J.* 2000, 19:4632-4643). These receptors are major drivers of tumorigenesis, and multiple targeted therapies that block EGFR and HER2 are approved by the FDA (see e.g., Slamon et al, *New England Journal of Medicine*, 2001, 344:783-792). Often, however, therapies that target EGFR and HER2 are only transiently effective due to a subsequent increase in membrane HER3 expression (see e.g., Sergina et al, *Nature*, 2007, 445:437-441). Upregulation of HER3 expression and transphosphorylation leads to escape from therapeutic inhibition through the PI3K/AKT pathway, rendering initial targeted therapy ineffective. Although HER3 has been less explored historically due to its mutated kinase domain, concurrent discoveries that its intracellular domain can in fact signal through transphosphorylation and that it is over-expressed in patients with resistance to a number of targeted therapies have brought it to the forefront of targeted therapy development (see e.g., Shi et al, *Proceedings of the national Academy of Sciences*, 2010, 107:7692-7697). In fact, HER3-mediated therapeutic resistance may not be limited to therapies that target EGFR or HER2, as evidence has emerged to link HER3 with castration resistant prostate cancer as well.

The role of HER3 in targeted therapy resistance has been well documented, and efforts to pharmacologically inhibit its activity are currently being explored. Clinical trials examining the efficacy of anti-HER3 antibodies including patritumab (NCT0213401S), MM-121 (NCT00734305), U3-1402 (NCT02980341), and GSK2849330 (NCT0196644S) are ongoing or have been completed recently, with limited success to date. One limiting factor for the administration of such agents is identifying patient populations most likely to benefit from the therapy. HER3 is particularly challenging to quantify by biopsy, because of its highly heterogeneous temporal and spatial expression. As drug approval continues to trend toward including a companion diagnostic with novel targeted therapies, an accurate method to quantify expression of HER3 to guide therapy is of paramount importance. PET imaging, which provides a global and repeatable methodology to assess target expression, is highly compatible with HER3 expression diagnosis. In order to facilitate such an assay, the present application provides a novel HER3 peptide for quantitative PET imaging of HER3 expressing tumors in murine models of multiple cancers. As described herein, the novel HER3 peptide, HER3P1, represents an accurate, pharmacokinetically favorable peptide imaging agent for HER3. HER3 represents a critical protein in targeted therapies for a number of cancers and its highly dynamic expression requires an equally dynamic approach to quantification. HER3 imaging with HER3P1 may represent a method to quantify HER3 and provide critical cellular feedback analysis.

Compositions

The present application provides, a composition of Formula I:

A-B-C    I wherein:
A comprises an imaging agent;
B is a linking group or a covalent bond; and
C is a polypeptide comprising from about 9 to about 75 amino acids, wherein the polypeptide comprises an amino acid sequence having at least 90% sequence identity to:

(SEQ ID NO: 13)

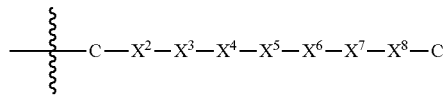

wherein:
∿∿∿∿ refers to the bond between C and B;
$X^2$ is selected from the group consisting of L, L*, I, I*, P, P*, V, V*, G, and G*;
$X^3$ is selected from the group consisting of P, P*, L, L*, I, I*, V, V*, G, and G*;
$X^4$ is selected from the group consisting of T, T*, S, S*, C, C*, M, and M*;
$X^5$ is selected from the group consisting of any L-amino acid, any D-amino acid, and any non-natural amino acid;
$X^6$ is selected from the group consisting of any L-amino acid, any D-amino acid, and any non-natural amino acid;
$X^7$ is selected from the group consisting of R, R*, H, H*, K, K*, N, N*, Q, and Q*, and
$X^8$ is selected from the group consisting of S, S*, T, T*, C, C*, M, and M*,
wherein:
L* is a non-natural derivative of L;
I* is a non-natural derivative of I;
P* is a non-natural derivative of P;
V* is a non-natural derivative of V;
G* is a non-natural derivative of G;
T* is a non-natural derivative of T;
S* is a non-natural derivative of S;
C* is a non-natural derivative of C;
M* is a non-natural derivative of M;
R* is a non-natural derivative of R;
H* is a non-natural derivative of H;
K* is a non-natural derivative of K;
N* is a non-natural derivative of N; and
Q* is a non-natural derivative of Q.

In some embodiments, A comprises an imaging agent selected from the group consisting of a paramagnetic ion, an x-ray imaging agent, a fluorophore, and a radioisotope.

In some embodiments, A comprises a paramagnetic ion. In some embodiments, the paramagnetic ion is selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), and erbium (III).

In some embodiments, A comprises an x-ray imaging agent. In some embodiments, the x-ray imaging agent is selected from the group consisting of lanthanum (III), gold (III), lead (II), bismuth (III), and iodinated x-ray imaging agents (e.g., diatrizoate, ioxaglate, metrizoate, iopamidol, iohexol, ioxilan, iopromide, iodixanol, and ioversol).

In some embodiments, A comprises a fluorophore. In some embodiments, the fluorophore is selected from the group consisting of Alexa 350, Alexa 430, AMCA, BODIPY 630/650, BODIPY 650/665, BODIPY-FL, BODPY-R6G, 13BODLPY-TMR, BODLPY-TRX, cascade blue, Cy3, Cy5, 6-FAM, fluorescein isothiocyanate, HEX, 6-JOE, oregon green 488, oregon green 500, oregon green 514, quantum dots, pacific blue, REG, rhodamine green, rhodamine red, renographin, ROX, TAMRA, TET, tetramethylrhodamine, Texas Red, the Alexafluor family, Cy5, Cy5.5, Cy7, indocyanine green (ICG), and fluorescent proteins (e.g., green fluorescent protein (GFP), red fluorescent protein (RFP), and dsRED).

In some embodiments, A comprises a radioisotope. In some embodiments, the radioisotope provided herein is useful as an imaging agent in one or more of the methods provided herein. In some embodiments, the radioisotope is suitable for PET imaging.

In some embodiments, the radioistope provided herein may also be useful in one or more therapeutic applications, for example, when administered to a subject in a therapeutically effective amount. For example, $^{131}$I and $^{64}$Cu may be useful as imaging agents (e.g., as non-toxic and/or non-therapeutic radioisotopes) when administered to the subject at low concentrations (e.g., 5 mCi) and may also be useful as therapeutic agents (i.e., as toxic radioisotopes and/or therapeutic radioisotopes) when administered to the subject at a higher concentration.

In some embodiments, the radioisotope is selected from the group consisting of $^3$H, $^{11}$C, $^{14}$C, $^{18}$F, $^{32}$P, $^{35}$S, $^{36}$Cl, $^{51}$Cr, $^{52}$Fe, $^{57}$Co, $^{58}$Co, $^{59}$Fe, $^{64}$Cu, $^{67}$Cu, $^{67}$Ga, $^{68}$Ga, $^{75}$Se, $^{76}$Br, $^{77}$Br, $^{89}$Zr, $^{90}$Y, $^{99m}$Tc, $^{111}$In, $^{123}$I, $^{124}$I, $^{125}$I, $^{131}$I, $^{152}$Eu, $^{153}$Sm, $^{166}$Ho, $^{177}$Lu, $^{186}$Re, $^{188}$Re, $^{201}$Tl, $^{203}$Pb, $^{210}$At, $^{211}$At, $^{212}$Bi, $^{213}$Bi, and $^{225}$Ac. In some embodiments, the radioisotope is selected from the group consisting of $^3$H, $^{11}$C, $^{14}$C, $^{18}$F, $^{35}$S, $^{52}$Fe, $^{58}$Co, $^{64}$Cu, $^{68}$Ga, $^{76}$Br, $^{77}$Br, $^{89}$Zr, $^{111}$In, $^{123}$I, $^{124}$I, $^{125}$I, $^{131}$I, $^{186}$Re, $^{188}$Re, and $^{201}$Tl. In some embodiments, the radioisotope is $^{68}$Ga.

In some embodiments, A further comprises a chelating agent. In some embodiments, the chelating agent is selected from the group consisting of 1,4,7-triazacyclononanetriacetic acid (NOTA), 1,4,7,10-tetraazacyclododecane-1,4,7,10-tetraacetic acid (DOTA), 1,4,7-triazacyclononane-1-glutaric acid-4,7-diacetic acid (NODAGA), ethylene diamine tetra-acetic acid (EDTA), diethylene triaminepentaacetic acid (DTPA), cyclohexyl-1,2-diaminetetraacetic acid (CDTA), ethyleneglycol-O,O'-bis(2-aminoethyl)-N,N,N',N'-tetraacetic acid (EGTA), N,N-bis(hydroxybenzyl)-ethylenediamine-N,N'-diacetic acid (HBED), triethylene tetramine hexaacetic acid (TTHA), hydroxyethylethylenediaminetriacetic acid (HEDTA), 1,4,8,11-tetraazacyclotetradecane-N,N',N'',N'''-tetraacetic acid (TETA), 1,4,7,10-tetraaza-1,4,7,10-tetra-(2-carbamoyl methyl)-cyclododecane (TCMC), and 2,2',2''-(2-(4-isothiocyanatobenzyl)-1,4,7-triazonane-1,4,7-triyl)triacetic acid (NOTA-NCS). In some embodiments, the chelating agent is selected from the group consisting of 1,4,7-triazacyclononanetriacetic acid (NOTA), 1,4,7,10-tetraazacyclododecane-1,4,7,10-tetraacetic acid (DOTA), 1,4,7-triazacyclononane-1-glutaric acid-4,7-diacetic acid (NODAGA), and 2,2',2''-(2-(4-isothiocyanatobenzyl)-1,4,7-triazonane-1,4,7-triyl)triacetic acid (NOTA-NCS). In some embodiments, the chelating agent is 1,4,7-triazacyclononanetriacetic acid (NOTA) or 2,2',2''-(2-(4-isothiocyanatobenzyl)-1,4,7-triazonane-1,4,7-triyl)triacetic acid (NOTA-NCS). In some embodiments, the chelating agent is 2,2',2''-(2-(4-isothiocyanatobenzyl)-1,4,7-triazonane-1,4,7-triyl)triacetic acid (NOTA-NCS). In some embodiments, the chelating agent is:

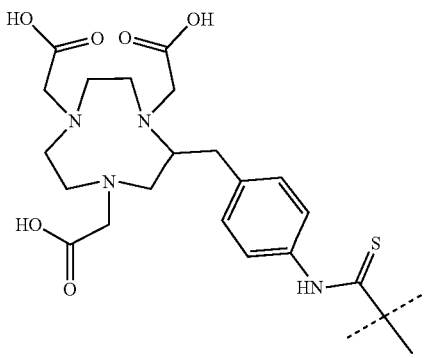

wherein ---- refers to the bond between A and B.

In some embodiments, B is a covalent bond. In some embodiments, B is a linking group.

In some embodiments, B is a linking group comprising one or more $C_{1-30}$ alkyleneoxy groups, one or more independently amino acids, or any combination thereof.

In some embodiments, B is a linking group comprising one or more $C_{1-30}$ alkyleneoxy groups. In some embodiments, B is a linking group comprising one or more —(OCH$_2$CH$_2$)— groups. In some embodiments, B is a linking group comprising one or more —(OCH$_2$CH$_2$)$_p$— groups, wherein p is an integer from 1 to 15, for example, 1 to 10, 1 to 5, 5 to 15, 5 to 10, or 10 to 15.

In some embodiments, B is a linking group comprising a combination of one or more $C_{1-30}$ alkyleneoxy groups and one or more independently selected amino acids.

In some embodiments, B is a linking group comprising one or more independently selected amino acids. In some embodiments, B is a linking group comprising from about 1 to about 20 independently selected amino acids, for example, about 1 to about 15, about 1 to about 10, about 1 to about 5, about 5 to about 20, about 5 to about 15, about 5 to about 10, about 10 to about 20, about 10 to about 15, or about 15 to about 20 independently selected amino acids. In some embodiments, B is a linking group comprising from about 1 to about 10 independently selected amino acids.

In some embodiments, B is a linking group comprising a sequence having at least 90% sequence identity to:

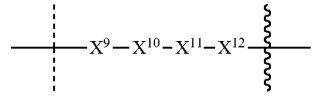

(SEQ ID NO: 2)

wherein:
------ refers to the bond between B and A;
∿∿∿∿ refers to the bond between B and C;
$X^9$ is selected from the group consisting of beta A, 6-aminohexnoic acid, 8-aminooctanoic acid, and 2-(2-(2-aminoethoxy) ethoxy) acetic acid;
$X^{10}$ is selected from the group consisting of G, G*, A, A*, S, S*, P, P*, W, W*, Y, Y*, H, H*, T, T*, M, M*, N, N*, Q, and Q*;
$X^{11}$ is selected from the group consisting of G, G*, A, A*, S, S*, P, P*, W, W*, Y, Y*, H, H*, T, T*, M, M*, N, N*, Q, and Q*; and
$X^{12}$ is selected from the group consisting of G, G*, A, A*, S, S*, P, P*, W, W*, Y, Y*, H, H*, T, T*, M, M*, N, N*, Q, and Q*;
wherein:
G* is a non-natural derivative of G;
A* is a non-natural derivative of A;
S* is a non-natural derivative of S;
P* is a non-natural derivative of P;
W* is a non-natural derivative of W;
Y* is a non-natural derivative of Y;
H* is a non-natural derivative of H;
T* is a non-natural derivative of T;
M* is a non-natural derivative of M;
N* is a non-natural derivative of N; and
Q* is a non-natural derivative of Q.

In some embodiments, $X^9$ is beta A.
In some embodiments, $X^{10}$ is G or G*. In some embodiments, $X^{10}$ is G.
In some embodiments, $X^{11}$ is G or G*. In some embodiments, $X^{11}$ is G.
In some embodiments, $X^{12}$ is G or G*. In some embodiments, $X^{12}$ is G.
In some embodiments, at least two of $X^{10}$, $X^{11}$, and $X^{12}$ are G or G*. In some embodiments, at least two of $X^{10}$, $X^{11}$, and $X^{12}$ are G.
In some embodiments, $X^9$ is beta A and at least two of $X^{10}$, $X^{11}$, and $X^{12}$ are G or G*. In some embodiments, $X^9$ is beta A and at least two of $X^{10}$, $X^{11}$, and $X^{12}$ are G.
In some embodiments, each of $X^{10}$, $X^{11}$, and $X^{12}$ are G or G*. In some embodiments, each of $X^{10}$, $X^{11}$, and $X^{12}$ are G.
In some embodiments, B is a linking group which is:

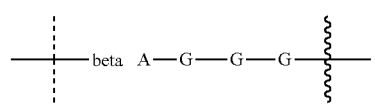

(SEQ ID NO: 3)

wherein:
------ refers to the bond between B and A; and
∿∿∿∿ refers to the bond between B and C.

In some embodiments, C is a polypeptide that binds HER3.

In some embodiments, C is a polypeptide comprising from about 9 to about 25 amino acids, wherein the polypeptide comprises an amino acid sequence having at least 90% sequence identity to SEQ ID NO: 13.

In some embodiments, C is a polypeptide comprising from about 9 to about 25 amino acids, wherein the polypeptide comprises an amino acid sequence having at least 90% sequence identity to SEQ ID NO: 12:

(SEQ ID NO: 12)

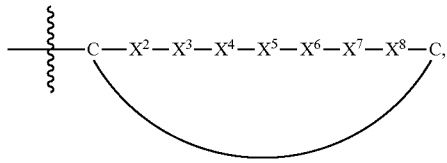

wherein the

refers to a disulfide bond between the cysteine groups (i.e., a cyclized amino acid sequence formed by the disulfide bond between the cysteine groups).

In some embodiments, $X^2$ is L or L*. In some embodiments, $X^2$ is L*. In some embodiments, $X^2$ is L.

In some embodiments, $X^3$ is P or P*. In some embodiments, $X^3$ is P. In some embodiments, $X^3$ is P*.

In some embodiments, $X^4$ is T or T*. In some embodiments, $X^4$ is T. In some embodiments, $X^4$ is T*.

In some embodiments, $X^5$ is K or K*. In some embodiments, $X^5$ is K. In some embodiments, $X^5$ is K*.

In some embodiments, $X^6$ is F or F*. In some embodiments, $X^6$ is F. In some embodiments, $X^6$ is F*

In some embodiments, $X^7$ is R or R*. In some embodiments, $X^7$ is R. In some embodiments, $X^7$ is R*

In some embodiments, $X^8$ is S or S*. In some embodiments, $X^8$ is S. In some embodiments, $X^8$ is S*.

In some embodiments:
$X^2$ is L or L*;
$X^3$ is P or P*;
$X^4$ is T or T*;
$X^5$ is K or K*;
$X^6$ is F or F*;
$X^7$ is R or R*; and
$X^8$ is S or S*.

In some embodiments:
$X^2$ is L;
$X^3$ is P;
$X^4$ is T;
$X^5$ is K;
$X^6$ is F;
$X^7$ is R; and
$X^8$ is S.

In some embodiments:
$X^2$ is L*;
$X^3$ is P*;
$X^4$ is T*;
$X^5$ is K*;
$X^6$ is F*;
$X^7$ is R*; and
$X^8$ is S*.

In some embodiments, the composition of Formula I is a composition of Formula Ia:

(SEQ ID NO: 4)

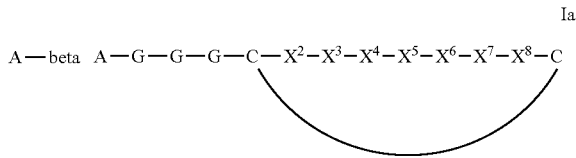

wherein $X^2$, $X^3$, $X^4$, $X^3$, $X^6$, $X^7$, and $X^8$ are defined according to the definitions provided herein for compositions of Formula I, and wherein

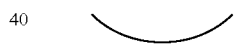

refers to a disulfide bond between the cysteine groups.

In some embodiments, the composition of Formula I is a composition of Formula Ib:

(SEQ ID NO: 5)

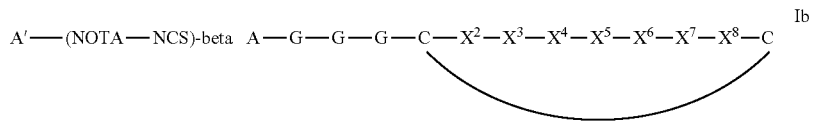

wherein:
A' is a radioisotope; and
$X^2, X^3, X^4, X^5, X^6, X^7$, and $X^8$ are defined according to the definitions provided herein for compositions of Formula I, and wherein

refers to a disulfide bond between the cysteine groups.

In some embodiments, the composition of Formula I is a composition of Formula Ic:

(SEQ ID NO: 6)

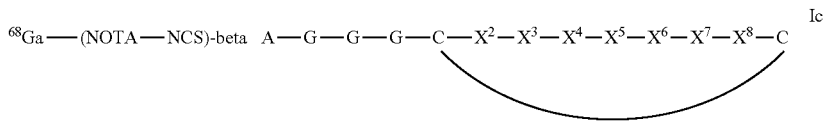  Ic wherein $X^2, X^3, X^4, X^5, X^6, X^7$, and $X^8$ are defined according to the definitions provided herein for compositions of Formula I, and wherein

refers to a disulfide bond between the cysteine groups.

In some embodiments, the composition of Formula I is:

(SEQ ID NO: 7)

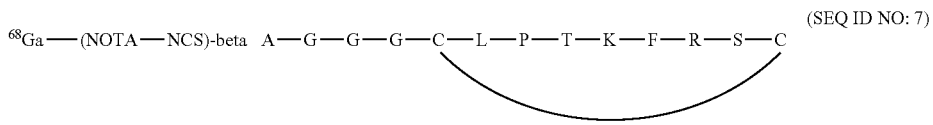

wherein

refers to a disulfide bond between the cysteine groups, wherein

In some embodiments, the composition of Formula I is a composition of Formula Id:

A-beta A-G-G-G-C-$X^2$-$X^3$-$X^4$-$X^5$-$X^6$-$X^7$-$X^8$-C (SEQ ID NO: 14)   Id wherein $X^2, X^3, X^4, X^5, X^6, X^7$, and $X^8$ are defined according to the definitions provided herein for compositions of Formula I.

In some embodiments, the composition of Formula I is a composition of Formula Ib:

A'-(NOTA-NCS)-beta A-G-G-G-C-$X^2$-$X^3$-$X^4$-$X^5$-$X^6$-$X^7$-$X^8$-C (SEQ ID NO: 15)   Ie wherein:
A' is a radioisotope; and
$X^2, X^3, X^4, X^5, X^6, X^7$, and $X^8$ are defined according to the definitions provided herein for compositions of Formula I.

In some embodiments, the composition of Formula I is a composition of Formula Ic:

6°Ga-(NOTA-NCS)-beta A-G-G-G-C-$X^2$-$X^3$-$X^4$-$X^5$-$X^6$-$X^1$-$X^8$-C(SEQ ID NO: 16)   If wherein $X^2, X^3, X^4, X^5, X^6, X^7$, and $X^8$ are defined according to the definitions provided herein for compositions of Formula I.

In some embodiments, the composition of Formula I is:

$^{68}$Ga-(NOTA-NCS)-beta A-G-G-G-C-L-P-T-K-F-R-S-C(SEQ ID NO: 17).

Compositions of Formula II

The present application further provides a composition of Formula II:

B-C   II

B comprises from about 1 to about 10 amino acids; and
C is a polypeptide comprising from about 9 to about 75 amino acids as defined herein for compositions of Formula I.

In some embodiments of Formula II, B comprises a sequence having at least 90% sequence identity to:

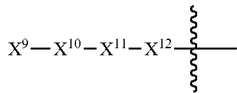

(SEQ ID NO: 26)

wherein:

∿∿∿ refers to the bond between B and C; and
wherein $X^9$, $X^{10}$, $X^{11}$, and $X^{12}$ are defined according to the definitions provided above for compositions of Formula I.

In some embodiments, $X^9$ is beta A.

In some embodiments, $X^{10}$ is G or G*. In some embodiments, $X^{10}$ is G.

In some embodiments, $X^{11}$ is G or G*. In some embodiments, $X^{11}$ is G.

In some embodiments, $X^{12}$ is G or G*. In some embodiments, $X^{12}$ is G.

In some embodiments, at least two of $X^{10}$, $X^{11}$, and $X^{12}$ are G or G*. In some embodiments, at least two of $X^{10}$, $X^{11}$, and $X^{12}$ are G.

In some embodiments, $X^9$ is beta A and at least two of $X^{10}$, $X^{11}$, and $X^{12}$ are G or G*. In some embodiments, $X^9$ is beta A and at least two of $X^{10}$, $X^{11}$, and $X^{12}$ are G.

In some embodiments, each of $X^{10}$, $X^{11}$, and $X^{12}$ are G or G*. In some embodiments, each of $X^{10}$, $X^{11}$, and $X^{12}$ are G.

In some embodiments, B is:

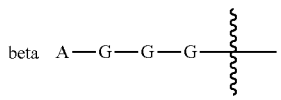

(SEQ ID NO: 9)

wherein ∿∿∿ refers to the bond between B and C.

In some embodiments, C is a polypeptide comprising from about 9 to about 25 amino acids, wherein the polypeptide comprises an amino acid sequence having at least 90% sequence identity to SEQ ID NO: 13. In some embodiments, C is a polypeptide comprising from about 9 to about 25 amino acids, wherein the polypeptide comprises an amino acid sequence having at least 90% sequence identity to SEQ ID NO: 12. In some embodiments, C is a polypeptide that binds HER3.

In some embodiments, $X^2$ is L or L*. In some embodiments, $X^2$ is L* In some embodiments, $X^2$ is L.

In some embodiments, $X^3$ is P or P*. In some embodiments, $X^3$ is P. In some embodiments, $X^3$ is P*

In some embodiments, $X^4$ is T or T*. In some embodiments, $X^4$ is T. In some embodiments, $X^4$ is T*

In some embodiments, $X^5$ is K or K*. In some embodiments, $X^5$ is K. In some embodiments, $X^5$ is K*

In some embodiments, $X^6$ is F or F*. In some embodiments, $X^6$ is F. In some embodiments, $X^6$ is F*.

In some embodiments, $X^7$ is R or R*. In some embodiments, $X^7$ is R. In some embodiments, $X^7$ is R*

In some embodiments, $X^8$ is S or S*. In some embodiments, $X^8$ is S. In some embodiments, $X^8$ is S*.

In some embodiments:
$X^2$ is L or L*;
$X^3$ is P or P*;
$X^4$ is T or T*;
$X^5$ is K or K*;
$X^6$ is F or F*;
$X^7$ is R or R*; and
$X^8$ is S or S*.

In some embodiments:
$X^2$ is L;
$X^3$ is P;
$X^4$ is T;
$X^5$ is K;
$X^6$ is F;
$X^7$ is R; and
$X^8$ is S.

In some embodiments:
$X^2$ is L*;
$X^3$ is P*;
$X^4$ is T*;
$X^5$ is K*;
$X^6$ is F*;
$X^7$ is R*; and
$X^8$ is S*.

In some embodiments, the composition of Formula II is a composition of Formula IIa:

(SEQ ID NO: 10)

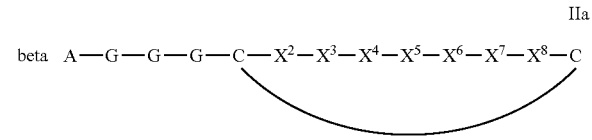

IIa wherein $X^2$, $X^3$, $X^4$, $X^5$, $X^6$, $X^7$, and $X^8$ are defined according to the definitions provided herein for compositions of Formula II, and wherein

refers to a disulfide bond between the cysteine groups.

In some embodiments, the composition of Formula II is a composition of Formula IIb:

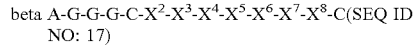

beta A-G-G-G-C-$X^2$-$X^3$-$X^4$-$X^5$-$X^6$-$X^7$-$X^8$-C(SEQ ID NO: 17)

IIb wherein $X^2$, $X^3$, $X^4$, $X^5$, $X^6$, $X^7$, and $X^8$ are defined according to the definitions provided herein for compositions of Formula II.

In some embodiments, the composition of Formula II is:

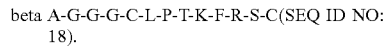

beta A-G-G-G-C-L-P-T-K-F-R-S-C(SEQ ID NO: 18).

In some embodiments, the composition of Formula II is:

(SEQ ID NO: 11)

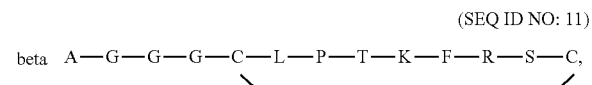

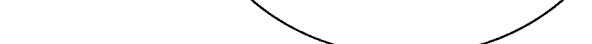

wherein

refers to a disulfide bond between the cysteine groups, wherein

Polypeptides that Bind HER3

The present application further provides a polypeptide suitable for binding HER3. In some embodiments, the polypeptide comprises from about 9 to about 75 amino acids. In some embodiments, the polypeptide comprises an amino acid sequence having at least 90% sequence identity to:

C-X²-X³-X⁴-X⁵-X⁶-X⁷-X⁸-C(SEQ ID NO: 19)

wherein X², X³, X⁴, X⁵, X⁶, X⁷, and X⁸ are defined according to the definitions provided herein for compositions of Formula I.

In some embodiments, the polypeptide comprises from about 15 to about 25 amino acids, wherein the polypeptide comprises an amino acid sequence having at least 90% sequence identity to SEQ ID NO: 19. In some embodiments, the polypeptide comprises from about 15 to about 25 amino acids, wherein the polypeptide comprises an amino acid sequence having at least 90% sequence identity to SEQ ID NO: 20:

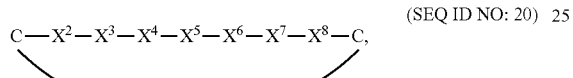
(SEQ ID NO: 20)

wherein

refers to a disulfide bond between the cysteine groups.

In some embodiments, X² is L or L* In some embodiments, X² is L*. In some embodiments, X² is L.

In some embodiments, X³ is P or P*. In some embodiments, X³ is P. In some embodiments, X³ is P*.

In some embodiments, X⁴ is T or T*. In some embodiments, X⁴ is T. In some embodiments, X⁴ is T*

In some embodiments, X⁵ is K or K*. In some embodiments, X⁵ is K. In some embodiments, X⁵ is K*

In some embodiments, X⁶ is F or F*. In some embodiments, X⁶ is F. In some embodiments, X⁶ is F*

In some embodiments, X⁷ is R or R*. In some embodiments, X⁷ is R. In some embodiments, X⁷ is R*

In some embodiments, X⁸ is S or S*. In some embodiments, X⁸ is S. In some embodiments, X⁸ is S*.

In some embodiments:
X² is L or L*;
X³ is P or P*;
X⁴ is T or T*;
X⁵ is K or K*;
X⁶ is F or F*;
X⁷ is R or R*; and
X⁸ is S or S*.

In some embodiments:
X² is L;
X³ is P;
X⁴ is T;
X⁵ is K;
X⁶ is F;
X⁷ is R; and
X⁸ is S.

In some embodiments:
X² is L*;
X³ is P*;
X⁴ is T*;
X⁵ is K*;
X⁶ is F*;
X⁷ is R*; and
X⁸ is S*

In some embodiments, the polypeptide is:

C-L-P-T-K-F-R-S-C(SEQ ID NO: 21).

In some embodiments, the polypeptide is:

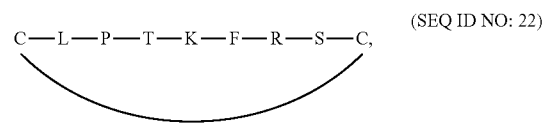
(SEQ ID NO: 22)

wherein

refers to a disulfide bond between the cysteine groups.

Synthesis

The compositions provided herein can be prepared, for example, according to the procedures described below.

Polypeptides

The compositions provided herein comprising polypeptides can be prepared, for example, using standard techniques for the preparation of peptide bonds (e.g., solid-phase synthetic techniques as described in Merrifield et al, *Journal of the American Chemical Society* 85.14 (1963): 2149-2154). Peptide synthetic techniques are well known to those of skill in the art and are described, for example, in Bodanszky et al, *Gastroenterology* 71 (1976): 965-970; Houghten, *Proceedings of the National Academy of Sciences* 82.15 (1985): 5131-5135; Stewart et al, Solid phase peptide synthesis. Pierce Chemical Company, 1984. Appropriate protective groups for use in such syntheses will be found in the above texts, as well as in McOmie, *Protective Groups in Organic Chemistry*, (1973): 98. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

In some embodiments, polypeptides of the present application may be prepared using solid phase synthetic techniques. For example, the amino acid is attached to an inert solid support through its unprotected carboxyl or amino group. The protecting group of the amino or carboxyl group is then selectively removed and the next amino acid in the sequence having the complementary (e.g., amino or carboxyl) group suitably protected is admixed and reacted with the residue already attached to the solid support. The protecting group of the amino or carboxyl group is then removed from the newly added amino acid residue, and a further amino acid (e.g. an appropriately protected amino acid) is then added. This procedure may be repeated until the desired polypeptide length has been prepared. After the desired amino acids have been linked in the proper sequence, any remaining terminal and side group protecting groups (and solid support) can be removed sequentially or concurrently to provide the final peptide. Additional reactions may be necessary, as described elsewhere, to form intramolecular linkages to restrain conformation.

Linking Groups

Bifunctional cross-linking reagents have been extensively used the preparation of affinity matrices, modification and stabilization of diverse structures, identification of ligand and receptor binding sites, and structural studies. Homobifunctional reagents having two identical functional groups have been shown to be highly efficient in cross-linking identical and different polypeptides or residues of a polypeptide, and the linking of polypeptide ligands to their specific binding sites. Heterobifunctional reagents contain two different functional groups. By taking advantage of differential reactivity of the different functional groups, cross-linking can be controlled both selectively and sequentially. For example, bifunctional cross-linking reagents can be divided according to the specificity of their functional groups, including, but not limited to, amino, sulfhydryl, guanidino, indole, carboxyl specific groups. Many heterobifunctional cross-linking reagents contain a primary amine-reactive group and a thiol-reactive group.

Additional examples of heterobifunctional cross-linking reagents and methods of using the cross-linking reagents are described in U.S. Pat. No. 5,889,155, the disclosure of which is incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. Table 1 details certain hetero-bifunctional cross-linkers considered useful for preparing compositions comprising a group B described herein (e.g., a linking group B as described herein).

TABLE 1

Hetero-Bifunctional Crosslinkers

| Linker | Reactive Toward | Advantages and Applications | Spacer Arm Length/ after cross-linking |
| --- | --- | --- | --- |
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

For compositions where a particular peptide does not contain a residue amenable for a particular cross-linking reagent in its native sequence, conservative genetic or synthetic amino acid changes in the primary sequence can be utilized.

Imaging Agents

Many appropriate imaging agents are known in the art, as are methods for their attachment to antibodies (see, for e.g., U.S. Pat. Nos. 5,021,236; 4,938,948; and 4,472,509, the disclosure of each of which is incorporated herein by reference in its entirety). Radioactively labeled compositions provided herein may be prepared according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. In a further example, compounds of Formula I provided herein may be labeled with $^{68}$Ga by radiometalation of a bifunctional chelator provided herein (e.g., NOTA, DOTA, NODAGA, or NOTA-NCS) or a similar derivative thereof.

Synthetic methods for incorporating radioisotopes into organic compounds are well known in the art, and one of ordinary skill in the art will readily recognize other methods applicable for the compounds provided herein.

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., March's *Advanced Organic Chemistry: Reactions, Mechanisms, and Structure*, 6$^{th}$ Ed. (Wiley, 2007); Trost et al. (Ed.), *Comprehensive Organic Synthesis* (Pergamon Press, 1991).

The reactions for preparing compositions described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

Preparation of compositions described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^{1}$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compositions can be purified by those skilled in the art by a variety of methods, including high performance liquid chromatography (HPLC) and normal phase silica chromatography.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Unless specifically defined, compounds and compositions provided herein can also include all isotopes of atoms occurring in the intermediates or final compounds. Isotopes include those atoms having the same atomic number but different mass numbers. Unless otherwise stated, when an atom is designated as an isotope or radioisotope (e.g., deuterium, [$^{11}$C], [$^{18}$F]), the atom is understood to comprise the isotope or radioisotope in an amount at least greater than the natural abundance of the isotope or radioisotope. For example, when an atom is designated as "D" or "deuterium", the position is understood to have deuterium at an abundance that is at least 3000 times greater than the natural abundance of deuterium, which is 0.015% (i.e., at least 45% incorporation of deuterium).

All compounds and compositions provided herein can be found together with other substances such as water and solvents (e.g. hydrates and solvates) or can be isolated.

In some embodiments, preparation of compounds and compositions described herein can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds (e.g., polypeptides) and compositions provided herein are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and compositions are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "non-natural amino acid" or "non-natural" refers to any derivative of a natural amino acid including D forms, and β and γ amino acid derivatives. It is noted that certain amino acids, e.g., hydroxyproline, that are classified as a non-natural amino acid herein, may be found in nature within a certain organism or a particular protein. In addition to the twenty most common naturally occurring amino acids, the following non-natural amino acids or amino acid derivatives may be constituents of the compositions described herein (common abbreviations are in parentheses): β-Alanine (beta A, β-Ala, βA, or β-A), γ-Aminobutyric Acid (GABA), 2-Aminobutyric Acid (2-Abu), α,β-Dehydro-2-aminobutyric Acid (A-Abu), 1-Aminocyclopropane-1-carboxylic Acid (ACPC), Aminoisobutyric Acid (Aib), 2-Amino-thiazoline-4-carboxylic Acid, 5-Aminovaleric Acid (5-Ava), 6-Aminohexanoic Acid (6-Ahx), 8-Aminooctanoic Acid (8-Aoc), 11-Aminoundecanoic Acid (11-Aun), 12-Aminododecanoic Acid (12-Ado), 2-Aminobenzoic Acid (2-Abz), 3-Aminobenzoic Acid (3-Abz), 4-Aminobenzoic Acid (4-Abz), 4-Amino-3-hydroxy-6-methylheptanoic Acid (Statine, Sta), Aminooxyacetic Acid (Aoa), 2-Aminotetraline-2-carboxylic Acid (Atc), 4-Amino-5-cyclohexyl-3-hydroxypentanoic Acid (ACHPA), para-Aminophenylalanine (4-NH2-Phe), Biphenylalanine (Bip), para-Bromophenylalanine (4-Br-Phe), ortho-Chlorophenylalanine (2-Cl-Phe), meta-Chlorophenylalanine (3-Cl-Phe), para-Chlorophenylalanine (4-Cl-Phe), meta-Chlorotyrosine (3-Cl-Tyr), para-Benzoylphenylalanine (Bpa), tert-Butylglycine (Tle), Cyclohexylalanine (Cha), Cyclohexylglycine (Chg), 2,3-Diaminopropionic Acid (Dpr), 2,4-Diaminobutyric Acid (Dbu), 3,4-Dichlorophenylalanine (3,4-Cl2-Phe), 3,4-Diflurophenylalanine (3,4-F2-Phe), 3,5-Diiodotyrosine (3,5-I2-Tyr), ortho-Fluorophenylalanine (2-F-Phe), meta-Fluorophenylalanine (3-F-Phe), para-Fluorophenylalanine (4-F-Phe), meta-fluorotyrosine (3-10 F-Tyr), Homoserine (Hse), Homophenylalanine (Hfe), Homotyrosine (Htyr), 5-Hydroxytryptophan (5-OH-Trp), Hydroxyproline (Hyp), para-Iodophenylalanine (4-I-Phe), 3-Iodotyrosine (3-I-Tyr), Indoline-2-carboxylic Acid (Idc), Isonipecotic Acid (Inp), metamethyltyrosine (3-Me-Tyr), 1-Naphthylalanine (1-Nal), 2-Naphthylalanine (2-Nal), para-Nitrophenylalanine, (4-NO2-Phe), 3-Nitrotyrosine (3-NO2-Tyr), Norleucine (Nle), Norvaline (Nva), Ornithine (Orn), ortho-Phosphotyrosine (H2PO3-Tyr), Octahydroindole-2-carboxylic Acid (Oic), Penicillamine (Pen), Pentafluorophenylalanine (F5-Phe), Phenylglycine (Phg), Pipecolic Acid (Pip), Propargylglycine (Pra), Pyroglutamic Acid (pGlu), Sarcosine (Sar), Tetrahydroisoquinoline-3-carboxylic Acid (Tic), and Thiazolidine-4-carboxylic Acid (Thioproline, Th). Stereochemistry of amino acids may be designated by preceding the name or abbreviation with the designation "D", "d", "L", or "l" as appropriate. Additionally, αN-alkylated amino acids may be employed, as well as amino acids having amine-containing side chains (such as Lys and Orn) in which the amine has been acylated or alkylated.

Methods of Use

The present application further provides methods of imaging HER3. In some embodiments, the method of imaging is performed in a cell, a tissue, a cell sample, a tissue sample, or a subject. As used herein, the term "subject," refers to any animal, including mammals and invertebrates. For example, mice, rats, other rodents, rabbits, dogs, cats, swine, cattle, sheep, horses, primates, fish, and humans. In some embodiments, the subject is a human. In some embodiments, the subject is a mouse. In some embodiments, the method comprises administering to the subject an effective amount of a composition provided herein (e.g., a composition of Formula I). In some embodiments, the method is an in vitro method. In some embodiments, the method is an in vivo method.

The present application provides a method of imaging cancer in a subject, the method comprising:
  i) administering to the subject an effective amount of a composition provided herein (e.g., a composition of Formula I); and
  ii) imaging the subject with a suitable imaging technique.

The present application further provides a method of treating a cancer in a subject, the method comprising:
  i) administering to the subject an effective amount of a composition provided herein (e.g., a composition of Formula I);
  ii) imaging the subject with a suitable imaging technique; and
  iii) administering to the subject a therapeutically effective amount of one or more therapeutic agents.

The present application further provides a method of monitoring treatment of a cancer in a subject, the method comprising:
  i) administering to the subject an effective amount of a composition provided herein (e.g., a composition of Formula I);

ii) imaging the subject with a suitable imaging technique; and iii) administering to the subject a therapeutically effective amount of one or more therapeutic agents.

In some embodiments, the methods provided herein further comprise administering an additional effective amount of the composition to the subject after step iii).

In some embodiments, the methods provided herein further comprise imaging the subject with a suitable imaging technique after step iii).

In some embodiments, the methods provided herein further comprise waiting a time sufficient to allow the compound to accumulate at a cell or tissue site (e.g., a cell or tissue site in a subject) associated with the disease, prior to imaging. In some embodiments, the methods provided herein further comprise waiting a time sufficient to allow the compound to bind HER3 at a cell or tissue site (e.g., a cell or tissue site in a subject) associated with the cancer, prior to imaging. In some embodiments, the time sufficient is from about 30 seconds to about 24 hours, for example, about 30 seconds to about 24 hours, about 30 seconds to about 12 hours, about 30 seconds to about 6 hours, about 30 seconds to about 2 hours, about 30 seconds to about 1 hour, about 30 seconds to about 30 minutes, about 30 seconds to about 10 minutes, about 10 minutes to about 24 hours, about 10 minutes to about 12 hours, about 10 minutes to about 6 hours, about 10 minutes to about 2 hours, about 10 minutes to about 1 hour, about 10 minutes to about 30 minutes, about 30 minutes to about 24 hours, about 30 minutes to about 12 hours, about 30 minutes to about 6 hours, about 30 minutes to about 2 hours, about 30 minutes to about 1 hour, about 1 hour to about 24 hours, about 1 hour to about 12 hours, about 1 hour to about 6 hours, about 1 hour to about 2 hours, about 2 hours to about 24 hours, about 2 hours to about 12 hours, about 2 hours to about 6 hours, about 6 hours to about 24 hours, about 6 hours to about 12 hours, or about 12 hours to about 24 hours.

In some embodiments, the cancer is a solid tumor. In some embodiments, the cancer is selected from the group consisting of breast cancer, lung cancer, prostate cancer, gastric cancer, head and neck cancer, and ovarian cancer. In some embodiments, the cancer is selected from the group consisting of breast cancer, lung cancer, and prostate cancer. In some embodiments, the cancer is prostate cancer. In some embodiments, the prostate cancer is castration resistant prostate cancer. In some embodiments, the cancer is breast cancer.

In some embodiments, the imaging technique is selected from the group consisting of magnetic resonance (MR) imaging, positron emission tomography (PET) imaging, fluorescent imaging, single photon emission computed tomography (SPECT), luminescent imaging, or any combination thereof. In some embodiments, the imaging technique is selected from the group consisting of magnetic resonance (MR) imaging, positron emission tomography (PET) imaging, or a combination thereof. In some embodiments, the imaging technique is positron emission tomography (PET) imaging.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

Combination Therapies

When employed in methods of treating or monitoring treatment of a disease, the compositions provided herein can be administered in combination with one or more of the additional therapeutic agents provided herein. Exemplary therapeutic agents include, but are not limited to, anesthetic agents (e.g., for use in combination with a surgical procedure), chemotherapeutic agents, and therapeutic antibodies.

In some embodiments, the additional therapeutic agent is an anesthetic agent. Exemplary anesthetic agents include, but are not limited to, local anesthetics (e.g., lidocaine, procain, ropivacaine) and general anesthetics (e.g., desflurane, enflurane, halothane, isoflurane, methoxyflurane, nitrous oxide, sevoflurane, mobarbital, methohexital, thiamylal, thiopental, diazepam, lorazepam, midazolam, etomidate, ketamine, propofol, alfentanil, fentanyl, remifentanil, buprenorphine, butorphanol, hydromorphone levorphanol, meperidine, methadone, morphine, nalbuphine, oxymorphone, pentazocine).

In some embodiments, the additional therapeutic agent is a chemotherapeutic agent. Exemplary chemotherapeutic agents include, but are not limited to, cisplatin, doxorubicin, taxol, etoposide, irinotecan, topotecan, paclitaxel, docetaxel, epothilones, tamoxifen, 5-fluorouracil, methotrexate, temozolomide, cyclophosphamide, tipifarnib, gefitinib, erlotinib, imatinib, gemcitabine, uracil mustard, chlormethine, ifosfamide, melphalan, chlorambucil, pipobroman, triethylenemelamine, busulfan, carmustine, lomustine, streptozocin, dacarbazine, floxuridine, cytarabine, 6-mercaptopurine, 6-thioguanine, fludarabine phosphate, oxaliplatin, folinic acid, pentostatin, vinblastine, vincristine, vindesine, bleomycin, dactinomycin, daunorubicin, epirubicin, idarubicin, mithramycin, deoxycoformycin, mitomycin-C, L-asparaginase, teniposide, neratinib, Sym013, cetrorelix, and enzalutamide.

Exemplary therapeutic antibodies include, but are not limited to, patritumab, lumretuzumab, trastuzumab, pertuzumab, MM-121, U3-1402, AV-203, and GSK2849330.

In some embodiments, the therapeutic agent is a HER3 inhibitor. In some embodiments, the therapeutic agent is selected from the group consisting of patritumab, MM-121, U3-1402, GSK2849330, neratinib, lumretuzumab, U3-1287, Sym013, AV-203, and erlotinib.

In some embodiments, the therapeutic agent is a HER2 inhibitor. In some embodiments, the HER2 inhibitor is selected from the group consisting of lapatinib, trastuzumab, pertuzumab, and erlotinib.

In some embodiments, the therapeutic agent is a PI3K inhibitor. In some embodiments, the PI3K inhibitor is GDC-0941.

In some embodiments, the therapeutic agent is a AKT inhibitor. In some embodiments, the AKT inhibitor is GDC-0068.

In some embodiments, the therapeutic agent is an androgen receptor antagonist. In some embodiments, the androgen receptor antagonist is enzalutamide.

In some embodiments, the therapeutic agent is a gonadotrophin-releasing hormone antagonist. In some embodiments, the gonadotrophin-releasing hormone antagonist is cetrorelix.

In some embodiments, the additional therapeutic agent is administered simultaneously with a composition provided herein. In some embodiments, the additional therapeutic agent is administered after administration of the composition provided herein. In some embodiments, the additional therapeutic agent is administered prior to administration of the composition herein. In some embodiments, the composition provided herein is administered during a surgical procedure. In some embodiments, the composition provided herein is administered in combination with an additional therapeutic agent during a surgical procedure.

The additional therapeutic agents provided herein can be effective over a wide dosage range and are generally administered in an effective amount. It will be understood, however, that the amount of the therapeutic agent actually administered will usually be determined by a physician, according to the relevant circumstances, including the condition to be imaged, the chosen route of administration, the actual compound administered, the age, weight, and response of the individual subject, the severity of the subject's symptoms, and the like.

Pharmaceutical Formulations

When employed as pharmaceuticals, the compositions and therapeutic agents provided herein can be administered in the form of pharmaceutical formulations. These formulations can be prepared as described herein or elsewhere, and can be administered by a variety of routes, depending upon whether local or systemic treatment is desired and upon the area to be treated. In some embodiments, the administration is selected from the group consisting of pulmonary administration (e.g., by inhalation or insufflation of powders or aerosols, including by nebulizer, intratracheal administration, or intranasal administration), oral administration, or parenteral administration (e.g., intravenous, intraarterial, subcutaneous, intraperitoneal, intramuscular or injection or infusion, intracranial, intrathecal, intraventricular administration, and the like). In some embodiments, the administration is intravenous or nasal administration.

Parenteral administration can be in the form of a single bolus dose, or may be, for example, by a continuous perfusion pump. Conventional pharmaceutical carriers, aqueous, powder, or oily bases, thickeners and the like, may be necessary or desirable.

Also provided are pharmaceutical formulations which contain, as the active ingredient, a composition provided herein in combination with one or more pharmaceutically acceptable carriers (excipients). In making a pharmaceutical formulation provided herein, the nanoparticle composition may be, for example, mixed with an excipient or diluted by an excipient. When the excipient serves as a diluent, it can be a solid, semi-solid, or liquid material, which acts as a vehicle, carrier, or medium for the nanoparticle composition. Thus, the pharmaceutical formulations can be in the form of powders, lozenges, elixirs, suspensions, emulsions, solutions, syrups, aerosols (as a solid or in a liquid medium), sterile injectable solutions, sterile packaged powders, and the like.

EXAMPLES

All chemicals and liquid solvents were obtained from Sigma-Aldrich (St. Louis, MO) unless otherwise stated. MDA-MB-453, HCC1954 and 22Rv1 cells were purchased from American Type Culture Collection (Manassas, VA) and cultured in RPMI-1640 media supplemented with 10% fetal bovine serum and 1% penicillin and streptomycin.

For comparison of phage clones against BSA and peptide specificity against other receptor tyrosine kinases, a one-way ANOVA with a Dunnett test to correct for multiple comparisons was performed. A sigmoidal dose response curve was fit to the peptide affinity data using Graphpad Prism 6.0. For peptide cell binding a two-way ANOVA with a Sidak's multiple comparisons test was performed. A linear regression was fit to HER3 TBR versus western blot data, with correlation significance calculated by a Pearson correlation. An unpaired t test was used to compare HER3 expression between 22RV1 and HCC-1954 tumors.

Example 1. Phage Display Selection

A cysteine-constrained randomized 7-mer library (New England Biolabs, Ipswich, MA) was utilized for the phage display selection. HER3 extracellular domain (ECD) (R&D Systems, Minneapolis, MN) was conjugated with long chain biotin (Thermo Scientific, Waltham, MA) utilizing standard NHS ester chemistry and purified by size exclusion chromatography with a 10 kDa molecular weight cut-off column (Genesee Scientific, San Diego, CA). Purified, biotinylated HER3 was bound to Dynabeads M-280 streptavidin beads (Thermo Scientific) and blocked with 1% non-fat dry milk in Tris-buffered saline (TBS) plus 0.1% Tween-20 (TBST). An aliquot of 2×1011 PFU phage were added to the beads and incubated for 1 hour at 37° C. Following incubation, beads were washed 10 times with TBST and eluted with 0.2 M glycine, pH 2.2 followed by neutralization with 1M Tris to pH 7.2 The output was then amplified in ER2738 *E. coli* (New England Biolabs) for 4.5 h at 37° C. followed and purified by the standard polyethylene glycol (PEG)/NaCl method (see e.g., Larimer and Deutscher, *American Journal of Nuclear Medicine and Molecular Imaging*, 2014, 4:435). The selection was performed for 3 rounds and following the third round individual phage plaques were picked for analysis by enzyme linked immunoabsorbent assay (ELISA).

Example 2. Individual Phage Characterization

Individually selected phages were amplified for 4.5 hours at 37° C. and supernatant was collected following centrifugation. HER3 ECD and bovine serum albumin as a control were adsorbed to Nunc Maxisorp 96 well plates (Sigma, St. Louis, MO). Supernatants corresponding to individual phages were added to HER3 and BSA wells and allowed to bind for 1 h at 37° C. Following binding, wells were washed 6 times with TBST and bound phage were detected by the addition of a horseradish peroxidase (HRP)-conjugated anti-M13 antibody. After a subsequent washing, 2,2'-azino-bis (3-ethylbenzothiazoline-6-sulfonic acid) (ABTS) substrate was added to wells and absorbance at 405 nm quantified by a Promega Glomax spectrophotometer (Promega, Madison, WI). The relative binding was compared to a control phage bearing no peptide and represented by the heat map in FIG. 1A. The phages with 5 best binding ratios of HER3 to BSA were chosen for amplification and purification to ensure no other supernatant factor was obscuring the signal. Following purification of the phages, ELISA was performed in the exact same manner and the absorbance of each phage to either HER3 or BSA was quantified by spectrophotometer. Phagemid DNA from each of the five phages in addition to three phages with no binding per the initial ELISA were recovered by plasmid miniprep isolation and automated Sanger DNA sequencing was performed by the CCIB DNA Core Facility at Massachusetts General Hospital (Cambridge, MA).

Each of these 5 phages had significantly higher background subtracted binding to HER3 as quantified by absorbance (range=0.177-0.253) than control phage, which had an absorbance of 0.007±0.002 (P<0.001), as shown in FIG. 1B. Given the significant specificity of each phage, all 5 were sequenced to ascertain the amino acid composition of their displayed peptide. Surprisingly, each of the sequenced phage displayed an identical peptide. To further confirm that the convergence of the selection was not resultant from a target unrelated peptide, three phage which did not demonstrate HER3 specific binding were also sequenced, and each had a different peptide sequence than the convergent sequence, as shown in FIG. 1C. Further in vitro characterization of the displayed peptide conjugated to biotin demonstrated high affinity binding of 270 nM to HER3, with greater than 4-fold specificity compared to other proteins, including the other similar receptor tyrosine kinases EGFR and HER2. Combined with specific binding of the peptide to HER3 expressing cancer cells, the peptide was selected for further in vivo analysis.

Example 3. In Vitro HER3 Affinity and Specificity Characterization

After determination of a consensus peptide binding sequence, the peptide sequence was covalently linked to a biotin-conjugated N-terminal tri-glycine linker using standard Fmoc chemistry. The purity and molecular weight were determined by high performance liquid chromatography and mass spectrometry. In order to confirm HER3 affinity, the peptide was analyzed for binding to HER3 ECD immobilized to Nunc Maxisorp 96 well microtiter plates. Following blocking with 1% non-fat dry milk, increasing concentrations of peptide were incubated with target protein for 1 h at 37° C. Wells were washed with 0.1% TBST, and bound peptide detected by addition of HRP-conjugated streptavidin (Abcam, Cambridge, UK), washing and ABTS substrate incubation for 10 minutes. Absorbance at 405 nm was read by spectrophotometer. In order to compare the specificity for HER3 against similar family members EGFR and HER2, extracellular domains of both EGFR and HER2 were immobilized and subjected to the same peptide ELISA at a single peptide concentration of 250 nM. Plates were washed and bound peptide once again detected by addition of streptavidin-HRP and ABTS and absorbance read at 405 nm.

Figures 2A, 2B:
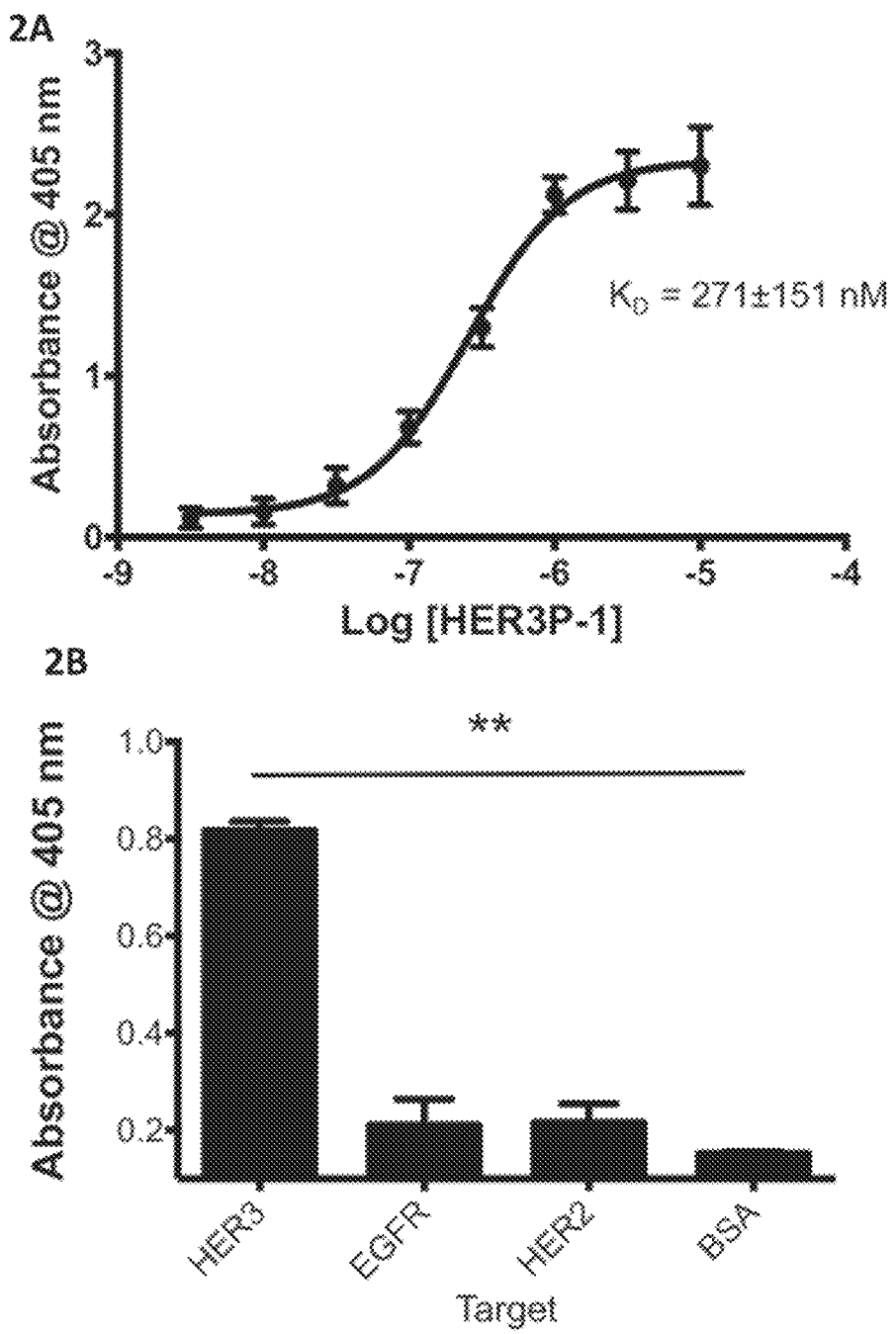
FIG. 2A shows peptide ELISA with increasing concentrations of HER3P1 demonstrates saturable binding and an affinity of 270 #151 nM. Triangles represent the mean of 6 replicates ±SEM.
FIG. 2B shows measured HER3P1 absorbance against two similar receptor tyrosine kinases and BSA, demonstrating approximately 4-fold selectivity over closely related proteins. Bars represent the mean of 6 replicates ±SEM. **P<0.01.

HER3P1 bound in a sigmoidal manner, with an affinity of 270±151 nM, as shown in FIG. 2A. The absorbance of HER3P1 binding to HER3 was 0.82=0.03, whereas binding to EGFR was 0.21±0.09, HER2 was 0.22=0.07 and BSA was 0.15=0.01 (P<0.001 for all), indicating that the peptide was highly specific for HER3 and suitable for cell binding analysis, as shown in FIG. 2B.

Example 4. HER3 Peptide Cellular Binding and Specificity Analysis

Two cell lines, MDA-MB-453 breast cancer cells which express moderate levels of HER3 and HCC-1954 cells which express low levels of HER3, were chosen to assess the ability of the peptide to discriminate between relatively close expression levels in vitro. Cells were seeded at a density of 1×10$^5$ cells/well in 96 well plates (Fisher) and grown overnight for 24 h in fetal bovine serum supplemented medium. HER3 peptide or a control peptide were added at 250 nM in media and incubated for 1 h at 37° C. Cells were washed 3× with PBS and bound peptide detected by addition of streptavidin-HRP. Cells were once again washed and bound peptide detected by addition of ABTS and absorbance read at 405 nm. Visual confirmation of peptide binding was confirmed by fluorescent microscopy. MDA-MB-453 and HCC-1954 cells were fixed in 10% formalin and dried onto microscope slides overnight. Following rehydration with TBS, slides were blocked with 2% BSA in TBS for 1 h prior to addition of peptide at a concentration of 250 nM in 0.1% TBST and incubation at room temperature for 1 h. Cells were washed 3× with 0.1% TBST and neutravidin-Alexafluor488 was added to cells and incubated at room temperature for 1 h. Cells were washed, mounted with Vectorshield mounting media with DAPI (Vector Labs, Burlingame, CA) and visualized by inverted microscope (Olympus, Tokyo, Japan).

Figures 3A, 3B, 3C:
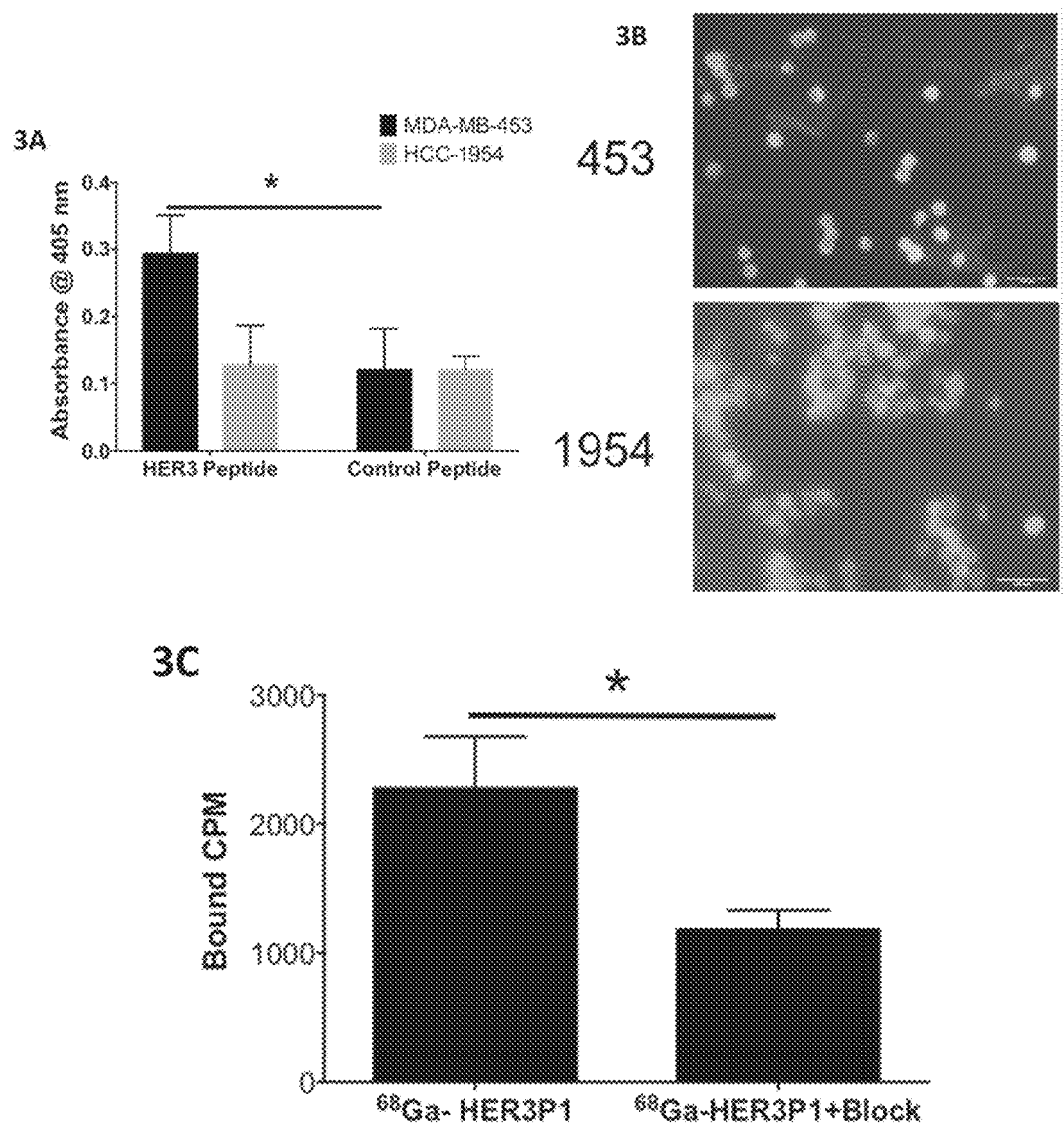
FIG. 3A shows quantitative measurement of HER3-1 binding to moderate (MDA_MB-453) and low (HCC-1954) HER3 expressing cells reveals significant differentiation by HER3P1 between cell types, in addition to significantly higher binding to a moderate HER3 cell line than a control peptide.
FIG. 3B shows fluorescent microscopy visualizes peptide binding to MDA-MB-453 cells, with little binding to HCC-1954 cells. *P<0.05.
FIG. 3C shows results of a $^{68}$Ga-HER3P1 (i.e., $^{68}$Ga-(NOTA-NCS)-HER3P1) competitive binding assay (P<0.05).

Cell binding for HER3P1 was quantified and absorbance for MDA-MB-453 was 0.29±0.06, whereas it was significantly lower for HCC-1954 cells 0.13=0.06 (P<0.05). Additionally HER3P1 binding was significantly higher to MDA-MB-453 cells than the control peptide (0.12±0.06, P<0.05), whereas there was no difference between the control peptide and the HER3Pl for binding to HCC-1954 cells, as shown in FIG. 3A. The strong selectivity of the peptide was also apparent using fluorescent microscopy, with high binding to MDA-MB-453 cells and almost no visualization of HCC-1954 cells, as shown in FIG. 3B.

Example 5. Positron Emission Tomography Imaging and Ex Vivo Correlation

To analyze whether the effective HER3 targeting in vitro could be recapitulated in vivo, a NOTA-NCS conjugated HER3 peptide was synthesized in the same manner as the biotinylated peptide, with NOTA-NCS being substituted for biotin. The peptide was radio labeled with the radiometal $^{68}$Ga eluted from a $^{68}$Ge/$^{68}$Ga generator (iThemba, South Africa) in 0.05M HCl. The pH of the elution was adjusted to approximately 4 by 2M=2-[4-(2-hydroxyethyl) piperazin-1-yl]ethanesulfonic acid and 100 ng of peptide reacted with the elution for 10 min at room temperature. Peptide was purified from free $^{68}$Ga by reverse phase C18 cartridge (Waters, Milford, MA) and purity determined by ITLC. The peptide was then prepared in normal saline to a specific activity of approximately 300 MBq/mg for injection into mice. Nu/nu mice bearing either 22RV1 (high HER3 expressing prostate cancer) or HCC-1954 (low HER3 expressing breast cancer) tumors were implanted in the right upper flank of mice and grown to approximately 5-7 mm. Radiolabeled HER3 peptide was injected intravenously and allowed to circulate for 1 h prior to PET imaging. PET images were acquired on an Inveon micro PET/CT (Siemens, Knoxville, TN) for 15 minutes in list mode, followed by CT acquisition. Images were constructed using 3D-MLEM (20 subsets) and corrected for scatter and randoms. The tumor and blood uptake was calculated in a 3D region of interest drawn around the tumor and heart, respectively, using CT guidance. Images were post-processed using VivoQuant (InviCRO, Boston, MA).

Following PET acquisition, tumors and relevant organs were removed from mice, weighed, and total activity for each was quantified by a Wallac gamma counter (Perkin Elmer, Waltham, MA). After radioactive decay, tumors were lysed and analyzed by Western blot for correlation of tumor uptake to HER3 expression normalized to β-actin. HER3 (sc-81455, Santa Cruz Biotech, Dallas, TX) and β-actin (13E5, Cell Signaling, Danvers, MA) antibodies were used to detect protein followed by an HRP-conjugated goat-anti-rabbit secondary antibody (Abcam) and detection by SignalFire chemiluminescent substrate (Cell Signaling). The specific activity of the labeled peptide was 296±25.9 MBq/mg.

Figure 4A:
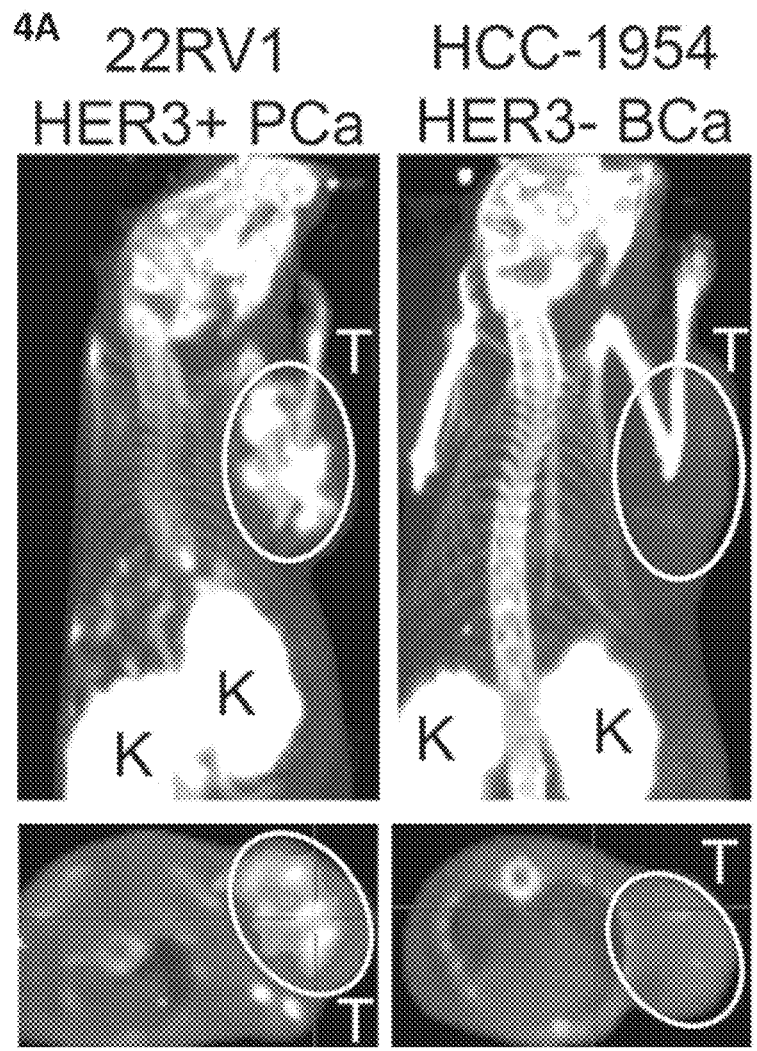
FIG. 4A shows sagittal and axial maximum intensity projections of the radiolabeled peptide ($^{68}$Ga-(NOTA-NCS)-HER3P1) in high HER3 expressing 22RV1 and low HER3 expressing HCC-1954 tumors. Peptide uptake is visualized in tumor and kidneys, which are the main route of clearance.

PET imaging demonstrated high $^{68}$Ga-(NOTA-NCS)-HER3P1 tumor uptake in 22RV1 tumor bearing mice, with much lower levels in HCC-1954 tumor bearing mice, as shown in FIG. 4A. Off-target peptide accumulation was minimal, with uptake in the kidneys and bladder consistent with the normal route of peptide clearance. Standardized tumor to blood ratios (TBR) for the high HER3 22RV1 ranged from 1.60 to 3.32 (n=4), whereas low HER3 HCC-1954 tumors ranged from 0.69 to 0.94 (n=4).

Figures 4B, 4C, 4D:
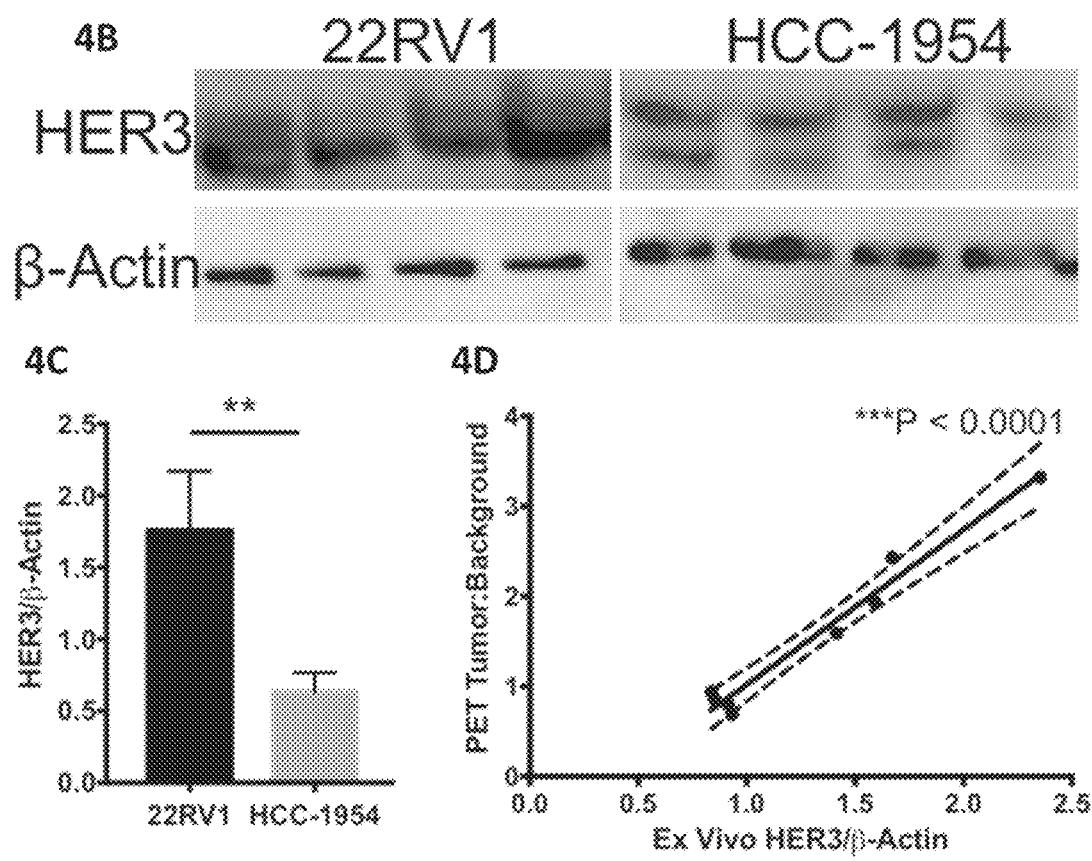
FIG. 4B shows western blot analysis of HER3 and β-actin for tumors excised from mice following PET imaging.
FIG. 4C shows quantification of HER3:β-actin ratio for 22RV1 and HCC-1954 tumors. Bars represent the mean of 4 replicates ±SEM.
FIG. 4D shows linear regression with 95% confidence intervals for each tumor comparing PET TBR to ex vivo HER3:β-actin ratio. Linear significance was determined by a Pearson's correlation. P<0.01, *p<0.0001.

Following PET acquisition, tumors were excised and HER3 and β-actin were quantified by Western blot, as shown in FIG. 4B. The HER3:β-actin ratio for each tumor was plotted against its corresponding TBR and fit to a linear regression with a goodness of fit $R^2$=0.96 and a Pearson correlation P value less than 0.0001. This data confirmed that the HER3P1 uptake was highly correlated with HER3 expression and accurately quantified total HER3 in vivo, as shown in FIG. 4C. Additionally, biodistribution analysis of HER3P1 was performed. Sites of accumulation included the HER3+ tumors (0.50±0.18% ID/g) and HER3+ organs such as the stomach (0.30±0.07% ID/g), intestines (0.48±0.15% ID/g) and lungs (0.70±0.14% ID/g), in addition to kidneys (10.1±1.67% ID/g) as a route of clearance, as shown in FIG. 5A. Accumulation in off-target organs was not due to blood accumulation, as tumor:organ ratios were significantly lower than tumor:blood ratios ($P<0.05$ stomach, $P<0.001$ intestines and lungs, as shown in FIG. 5B. Comparison between PET TBR and biodistribution TBR was highly correlated, as determined using a Pearson correlation ($P<0.001$), as shown in FIG. 5C.

HER3P1 demonstrated excellent tumor to background ratios (1.59-3.32) in HER3+ tumors which were significantly higher than the low HER3 expressing control tumors (0.84-0.93). Furthermore, ex vivo analysis of imaged tumors revealed a high ($P<0.001$) correlation between HER3 peptide uptake and both HER3 protein expression and percent injected dose per gram. These results indicate that HER3P1 represents a promising, clinically translatable HER3 imaging agent, and future translational efforts are being sought. PET imaging also revealed high tumor to blood ratios in the HER3 positive 22RV1 cell line, with background levels in HER3-negative HCC-1954 tumors. Furthermore, ex vivo analysis of the tumors used for PET imaging provided a highly significant correlation between protein expression and PET TBR, indicating an accurate and robust method of HER3 quantification suitable for exploration in both preclinical and clinical trials.

A competitive binding assay was also performed according to the following procedures. Ten μCi of purified $^{68}$Ga-HER3P1 was added to 1×10$^5$ MDA-MB-453 cells and incubated for 1 h. After incubation, cells were washed 3× with TBS and bound radioactivity quantified by a Wallac gamma counter (Perkin Elmer, Waltham, MA). As a control, excess (100 μM) peptide was added to cells and bound peptide measured in the same manner. The $^{68}$Ga-HER3P1 bound to MDA-MB-453 cells and binding was significantly ($P<0.05$) blocked by the addition of excess unlabeled (NOTA-NCS)-HER3P1, indicating specific peptide binding, as shown in FIG. 3C.

Example 6. Peptide Sequence Mapping

Figure 6:
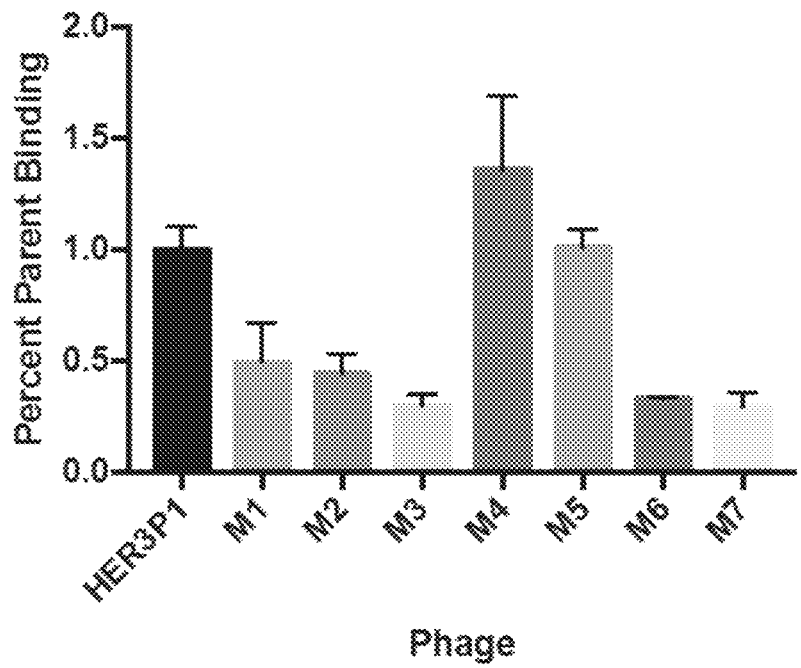
FIG. 6 shows mean phage binding normalized to parent (HER3P1) peptide. M1 corresponds to mutant in position 1 following the cysteine, which is position 2 of the binding sequence. Each of the subsequent phages (M2, M3, etc.) follow this naming convention. Bars represent the mean of 4 replicates with error bars denoting standard error measurements.

Parent peptide sequence C-L-P-T-K-F-R-S-C(SEQ ID NO.: 1) was mutated at positions 2-8 to an alanine, and binding of the phage to HER3 was assessed. The results, shown in FIG. 6, illustrate that for positions 2-4 and 7-8, substitution to alanine diminished binding to HER3 by 50% or greater. In contrast, positions 5-6 were unaffected by the mutation. This data demonstrates that amino acids 2-4 and 7-8 are involved in peptide binding, whereas 5 and 6 are amenable to mutation.

Example 7. In Vivo Analysis of Human Breast Cancer Xenografts

Figure 7:
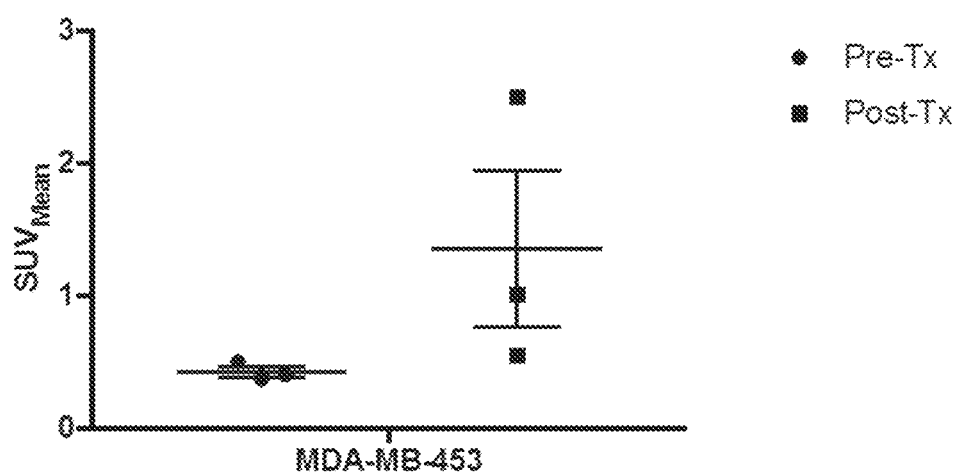
FIG. 7 shows the measured $SUV_{mean}$ of mice bearing MDA-MB-453 HER2+lapatinib resistant tumors were imaged pre-(circles) and post-therapy (squares) each point represents a matched pair of images from a single mouse imaged at day 0 pre-therapy and 2 days post therapy initiation. Bars represent mean and standard error measurement.
Figure 8:
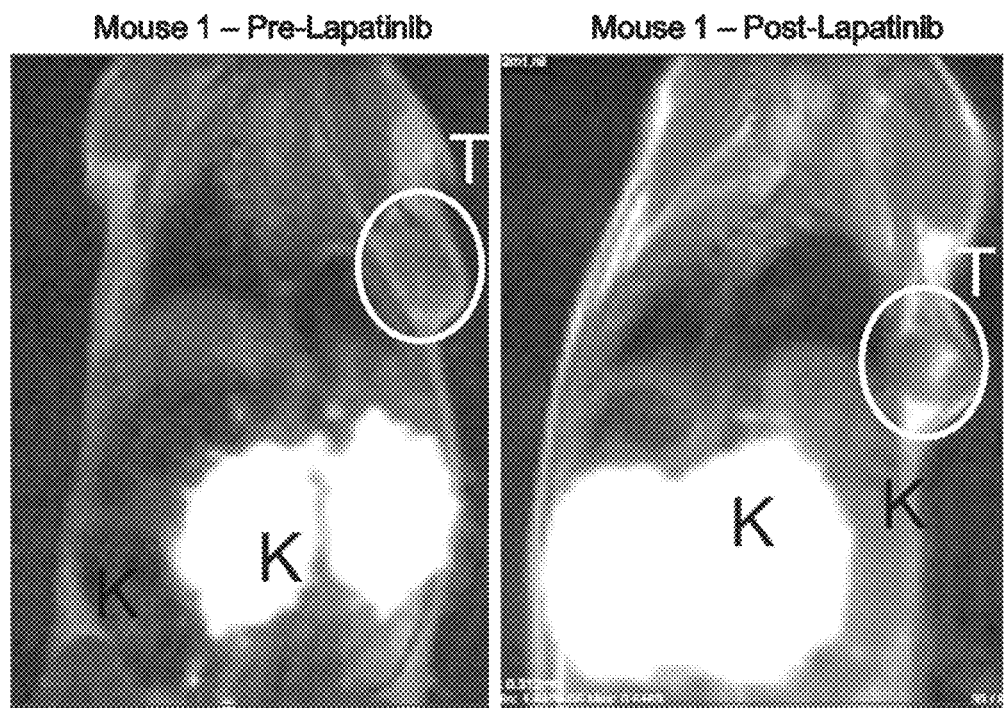
FIG. 8 shows representative PET/MR images of a single mouse (mouse 1) pre-lapatinib (left image) and 2 days post-lapatinib therapy (right image). Tumors are circled and labeled with a white (T). Kidneys, which are the main route of peptide clearance, are labeled with a black K.

In vivo analyses with HER3P1 have focused on utilizing the radiolabeled peptide to analyze human breast cancer xenografts before and after treatment with the receptor tyrosine kinase inhibitor lapatinib. In brief, mice bearing human MDA-MB-453 tumors were injected with $^{68}$Ga-(NOTA-NCS)-HER3P1 and subjected to PET imaging. Following imaging, mice were treated with 100 mg/kg of lapatinib every 12 hours for 48 hours following PET imaging. At the end of 48 hours, mice were imaged in the exact same manner as before treatment. Prior to therapy, mice bearing HER2+ breast cancer MDA-MB-453 tumors, which have previously been shown to develop resistance to therapy through HER3 upregulation, had uniformly low uptake as measured by HERP1 SUV$_{mean}$=0.42±0.04. Following lapatinib therapy, SUV$_{mean}$ levels of HER3P1 increased to 1.35±0.59, as shown in FIG. 7. Representative images from one of the mice is shown in FIG. 8.

Example 8. Noninvasive Assessment of HER3-Based Resistance to PI3K Targeted Therapy in Triple Negative Breast Cancer (TNBC)

Without being bound by theory, it is believed that HER3P1 PET imaging will allow for non-invasive quantification of HER3 receptor expression level changes in response to PI3K inhibition, facilitating rapid analysis of HER3 mediated resistance across a panel of triple negative breast cancers (TNBCs).

A panel of TNBC cell lines considered sensitive or resistant to PI3K inhibition with GDC-0941 (IC$_{50}$<1 μM) (Sensitive: HDQ-P1, CAL-51, HCC-70, CAL-148, HCC-1395, HS-578T, CAL-148; Resistant: MDA-MB-468, MDA-MB-231, MDA-MB-157, BT-549, CAL-120) (see e.g., O'Brien et al, *Clin Cancer Res.* 2010, 16:3670-3683) will be treated with GDC-0941. The selected cell lines are reflective of the genetic heterogeneity of TNBC, with all dominant genetic categories represented (PI3KCA mutations, PTEN loss, KRAS mutant, EGFR overexpression). The cell lines will be treated with the PI3K inhibitor GDC-0941 and Western blot will be used to assess expression and phosphorylation status of HER3, as well as downstream growth signaling proteins (PI3K, AKT, mTOR, S6K, ERK) to assess for persistent signaling after PI3K inhibition. In addition, whole cell viability and proliferation will also be analyzed using Celltiter-Glo. Eight cell lines will be selected for further in vivo analysis. Cell lines will include two sensitive cell line without HER3 upregulation, two sensitive cell line demonstrating HER3 upregulation, two resistant cell lines without HER3 upregulation after treatment, and two resistant cell lines with HER3 upregulation after treatment. Following in vitro biochemical analysis, xenografts of the selected tumors will be implanted in nu/nu female mice. Once tumors measure 5 mm in diameter, mice will be imaged by PET/CT with $^{68}$GA-HER3P1 (i.e., $^{68}$Ga-(NOTA-NCS) HER3P1), according to our previously established protocols (see e.g., Wehrenberg-Klee et al, *Journal of*

Nuclear Medicine, 2016, 57 (9): 1413-1419). Tumor to background and tumor to blood pool ratios will be calculated. Following initial imaging, mice will be randomized to 48 h treatment with 75 mg/kg GDC-0941 or vehicle. 48 h following treatment initiation, mice will be injected with $^{68}$Ga-HER3P1, and PET imaged again as described above. To confirm accurate quantification of HER3 expression by our HER3 PET probe, as well as similar biochemical response to PI3K inhibition in vivo as defined during in vitro cell analysis, mice will be sacrificed following final imaging and tumors harvested. Radioactivity of excised tumors will be immediately measured by gamma counter. Following radioactive decay, tumor will be homogenized, lysed and the tumor lysate analyzed by Western blot as above.

Example 9. Using Imaged HER3 Upregulation Patterns, Test Efficacy of HER3 Inhibitor Addition to Inhibit TNBC Growth In Vitro and In Vivo From the eight cell lines identified for HER3 PET imaging in Example 8, a subset of four cell lines including one sensitive cell line without HER3 upregulation, one sensitive cell line demonstrating HER3 upregulation, one resistant cell line without HER3 upregulation after treatment, and one resistant cell line with HER3 upregulation after treatment will be analyzed in order to correlate imaging findings to proliferation and growth responses. Each cell line will be treated with PI3K inhibitor, PI3K inhibitor with additional HER3 inhibitor, or vehicle. Efficacy of treatment regimens overtime will be assessed with viability (MTT, Presto Blue, WST-1) and clonogenic (Crystal violet) assays. Growth pathway inhibition will be assessed by Western blot. The same cell lines selected for in vitro analysis will also be analyzed in vivo. Female nu/nu mice bearing cell line xenografts will be treated with vehicle, single agent PI3K inhibitor, or PI3K inhibitor with the addition of HER3 inhibitor. Tumor volumes will be measured three times a week. Experiments will terminate when significant differences in tumor growth are recorded between the treatment arms and/or the tumor volumes reach size requiring euthanasia. These experiments will also inform on treatment tolerability. Tumors will be harvested at the end of the experiments to confirm target inhibition. Conventionally, we will always collect tissue samples two hours from the last drug administration to allow both intra- and inter-experimental comparisons. When possible (xenografts are not too small and/or fibrotic), samples will be analyzed by Western blot against the total and phosphorylated forms of the targeted RTKs and signaling pathway effectors (phospho-AKT, phosphoPRAS40, phosphoS6K, phospho4EBP1). Moreover, the same analyses will be validated by immunohistochemistry (IHC). IHC will also be used to measure the nuclear/cytosolic ratio of FOXO, a known transcription factor responsible for HER3 upregulation upon PI3K inhibition.

Example 10. TNBC Patient-Derived Xenograft HER3 PET Imaging and Treatment with PI3K Inhibitor and Image Guided Therapy For PDX establishment, fresh tissue previously obtained from either the Massachusetts General Hospital or Memorial Sloan Kettering Cancer Center under Institutional Review Board approval and patients' informed consent will be utilized and tissues will be completely deidentified. Formalin-fixed paraffin-embedded (FFPE) specimens for IHC analyses of EGFR and HER3 abundance were obtained from participating institutions, as described previously (see e.g., García et al, *Clinical Cancer Research,* 2012, 18:2603-2612; Tao, J. J et al, *Science signaling,* 2014, 7 (318): ra29; and Bosch, A. et al, *Science translational medicine,* 2015 7 (283): 283ra51-283ra51). Four TNBC PDX lines will be utilized. Female nude mice bearing PDXs will be used to implant subsequent mice for all studies. Tumors will be imaged with $^{68}$Ga-HER3P1 and randomized to treatment with GDC-0941 (PI3K inhibitor) or vehicle. Following two days of treatment, the mice will undergo repeat $^{68}$Ga-HER3P1 imaging, as previously described, and tumoral HER3 PET SUV will be measured. The GDC-0941 group will then be randomized to receive additional HER3 inhibitor or additional vehicle. Following the initiation of secondary treatment, tumor volumes will be measured by caliper at least three times a week. Experiments will be carried out for 35 days following the beginning of secondary treatment, or when the tumor volumes reach unethical size. Tumors will be harvested at the end of the experiments to confirm target inhibition. In the same manner as with xenografted cell lines, samples will be analyzed ex vivo by Western blot when possible against the total and phosphorylated forms of HER3 as well as downstream signaling proteins as described above. IHC samples will also be analyzed following previously described technique.

Example 11. Analysis and Imaging of HER3 and Downstream Signaling Pathways in TNBC Cell Lines A panel of TNBC cell lines considered sensitive or resistant to AKT inhibition with GDC-0068 ($IC_{50}$<1 µM) (Sensitive: CAL-148, HCC-70, CAL-51, HCC-1395, HS-578T; Resistant: MDA-MB-468, HC-143, CAL-85-1, HDQ-P1, MDA-MB-231, BT-549) 4,37 will be treated with GDC-0068. The identical cell signaling and viability assays performed in Examples 8-10, will be performed in Example 11 to compare the effects of AKT inhibition. For each therapy, four cell lines will be selected for further in vivo analysis. Cell lines will include a sensitive cell line without HER3 upregulation, a sensitive cell line demonstrating the most HER3 upregulation, a resistant cell line without HER3 upregulation after treatment, and a resistant cell line with HER3 upregulation after treatment. Following in vitro biochemical analysis, xenografts of the selected tumors will be implanted in nu/nu female mice and PET images will be acquired and data analyzed in the same manner as detailed in Examples 8-10. Following imaging, mice will be randomized to 48 h treatment with 75 mg/kg GDC-0068 or vehicle. 48 h following treatment initiation, mice will be injected with $^{68}$Ga-HER3P1 and again imaged with image analysis as per Example 8. To confirm accurate quantification of HER3 expression by our HER3 PET probe, as well as similar biochemical response to AKT inhibition in vivo as defined during in vitro cell analysis, mice will be sacrificed, tumors harvested and the tumor lysate analyzed by Western blot as above.

Example 12. Imaged HER3 Upregulation Patterns in Response to AKT Inhibition, Test Efficacy of HER3 Inhibitor Addition to Inhibit TNBC Growth Both In Vitro and In Vivo From the eight cell lines identified for HER3 PET imaging in Example 11, a subset of four cell lines including one sensitive cell line without HER3 upregulation, one sensitive cell line demonstrating HER3 upregulation, one resistant cell line without HER3 upregulation after treatment, and one resistant cell line with HER3 upregulation after treatment will be analyzed in order to correlate imaging findings to proliferation and growth responses. In vitro studies of treatment efficacy for HER3 inhibitor combination therapies will be systematically conducted as in Example 9. The same cell lines selected for in vitro analysis will also be analyzed in vivo. Female nu/nu mice bearing cell line xenografts will be treated with vehicle, single agent AKT inhibitor, or AKT inhibitor with the addition of HER3 inhibitor. Tumor volumes will be measured and following completion of study excised tumors will be assessed as in Example 9.

Example 13. TNBC PDX Tumor HER3 PET Imaging and Adaptive Therapy Following AKT Inhibition Four TNBC PDX lines will be utilized, as outlined in Example 10. Tumors will be imaged with HER3P1 and then randomized to treatment with the AKT inhibitor GDC-0068 75 mg/kg or vehicle. Following two days of treatment, the mice will undergo repeat imaging, as previously described, and tumoral HER3 PET SUV will be measured. GDC-0068 treated tumors will then be randomized to receive HER3 inhibitor therapy or vehicle. Following the initiation of secondary treatment, tumor volumes will be measured for 35 days following the beginning of secondary treatment, or when the tumor volumes reach unethical size. Tumors will be harvested at the end of the experiments to confirm target inhibition. In the same manner as with xenografted cell lines, samples will be analyzed ex vivo by Western blot when possible against the total and phosphorylated forms of HER3 as well as downstream signaling proteins as described above. IHC samples will also be analyzed following previously described technique.

Example 14. Changes in HER3 Expression in HER2+ Breast Cancer Following Lapatinib Treatment HER2+ breast cancer cell lines, either sensitive to HER2 inhibition (BT-474, SKBR3, UACC812, UACC893, ZR-75-30) 47 or resistant to HER2 inhibition (JIMT-1, MDA-MB-453, HCC1569, HCC1954, MDA-MB-361) (see e.g., Wang et al, Breast Cancer Res. 2011, 13: R121), and including the dominant mutations found in HER2+ breast cancer (PI3KCA mutations, PTEN loss) will be treated with standard treatment dose of the HER2 inhibitor lapatinib (1 µM) or vehicle for 48 h. Following treatment, expression and phosphorylation status of HER3 and HER2 as well as downstream growth signaling proteins PI3K, AKT, mTOR, S6K, ERK will be assessed by Western blot, and quantified as described above. Cell viability (Celltiter-Glo) assays will be performed to monitor the effects of lapatinib treatment on proliferation. After in vitro analysis, a total of four cell lines will be selected for further in vivo imaging analysis. The identical cell signaling and viability assays performed in Examples 8-10, will be performed in this Example to compare the effects of AKT inhibition. For each therapy, four cell lines will be selected for further in vivo analysis. Cell lines will include a sensitive cell line without HER3 upregulation, a sensitive cell line demonstrating the most HER3 upregulation, a resistant cell line without HER3 upregulation after treatment, and a resistant cell line with HER3 upregulation after treatment. Following in vitro biochemical analysis, xenografts of the selected tumors will be implanted in nu/nu female mice, randomized to 48 h treatment with lapatinib or vehicle. Following treatment initiation, mice will be injected with dose of HER3 PET Probe. PET imaging data will be obtained and analyzed as described in Examples 8-10. Tumors will be excised and tumor and analyzed by Western blot for expression and phosphorylation of HER3 and downstream signaling proteins as described for in vitro studies.

Example 15. Efficacy of HER3 Inhibitor Therapy Addition to HER2 Inhibitor Therapy The four cell lines identified for HER3 PET imaging in Example 14 will be used for treatment experiments. For each cell line, in vitro studies of treatment efficacy for HER3 inhibitor and HER2 inhibitor combination regimens will be conducted in the same manner as Examples 9 and 12. Following in vitro analysis, groups of female nu/nu mice bearing cell-line xenografts will be treated with control, lapatinib, or the combination of lapatinib and HER3 inhibitor, tumor volumes measured, and when possible tumors excised an analyzed ex vivo to determine the molecular signatures of effective therapy and resistance outlined in Example 14.

Example 16. HER2+ PDX HER3 PET Imaging to Guide Adaptive Therapy

Four HER2+ PDX lines will be established in a manner similar to Examples 10 and 13. Female nude mice bearing PDXs will be PET imaged and then randomized to treatment with lapatinib or vehicle. Following two days of treatment, the mice will be undergo repeat HER3 PET imaging. The lapatinib arm will then be further randomized to receive either HER3 inhibitor therapy in addition to previously assigned therapy, or additional vehicle. Following the initiation of secondary treatment, tumor volumes will be measured by caliper three times a week. Experiments will be carried out for 35 days following the beginning of secondary treatment, or when the tumor volumes reach unethical size. Tumors will be harvested at experiment end to confirm target inhibition. Samples will be analyzed ex vivo by Western blot when possible against the total and phosphorylated forms of HER3 as well as downstream signaling proteins as described above. IHC samples will also be analyzed following previously described technique.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition of Formula II:

B-C, wherein:
B comprises a sequence:

(SEQ ID NO: 8)

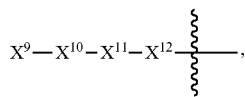

and
C comprises a sequence:

(SEQ ID NO: 12)

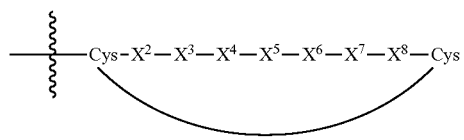

wherein:

is a disulfide bond between the cysteine groups, and wherein the polypeptide comprises from about 9 to about 75 amino acids;

∽∽∽ is a bond between B and C;

$X^2$ is selected from the group consisting of L, L*, I, I*, P, P*, V, V*, G, and G*;

$X^3$ is selected from the group consisting of P, P*, L, L*, I, I*, V, V*, G, and G*;

$X^4$ is selected from the group consisting of T, T*, S, S*, C, C*, M, and M*;

$X^5$ is selected from the group consisting of any L-amino acid, any D-amino acid, and any non-natural amino acid;

$X^6$ is selected from the group consisting of any L-amino acid, any D-amino acid, and any non-natural amino acid;

$X^7$ is selected from the group consisting of R, R*, H, H*, K, K*, N, N*, Q, and Q*;

$X^8$ is selected from the group consisting of S, S*, T, T*, C, C*, M, and M*;

$X^9$ is selected from the group consisting of beta A, 6-aminohexanoic acid, 8-aminooctanoic acid, and 2-(2-(2-aminoethoxy) ethoxy) acetic acid;

$X^{10}$ is selected from the group consisting of G, G*, A, A, S, S*, P, P*, W, W*, Y, Y*, H, H*, T, T*, M, M*, N, N*, Q, and Q*;

$X^{11}$ is selected from the group consisting of G, G*, A, A, S, S*, P, P*, W, W*, Y, Y*, H, H*, T, T*, M, M*, N, N*, Q, and Q*;

$X^{12}$ is selected from the group consisting of G, G*, A, A, S, S*, P, P*, W, W*, Y, Y*, H, H*, T, T*, M, M*, N, N*, Q, and Q*;

wherein:
L* is a non-natural derivative of L;
I* is a non-natural derivative of I;
P* is a non-natural derivative of P;
V* is a non-natural derivative of V;
G* is a non-natural derivative of G;
T* is a non-natural derivative of T;
S* is a non-natural derivative of S;
C* is a non-natural derivative of C;
M* is a non-natural derivative of M;
R* is a non-natural derivative of R;
H* is a non-natural derivative of H;
K* is a non-natural derivative of K;
N* is a non-natural derivative of N;
Q* is a non-natural derivative of Q;
A* is a non-natural derivative of A;
W* is a non-natural derivative of W; and
Y* is a non-natural derivative of Y.

2. The composition of claim 1, wherein B is:

(SEQ ID NO: 9)

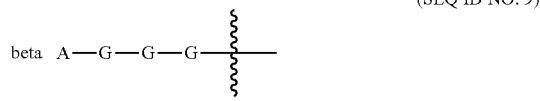

wherein ∿∿∿ refers to the bond between B and C.

3. The composition of claim 1, wherein $X^2$ is L or L*.
4. The composition of claim 1, wherein $X^3$ is P or P*.
5. The composition of claim 1, wherein $X^4$ is T or T*.
6. The composition of claim 1, wherein $X^5$ is K or K*.
7. The composition of claim 1, wherein $X^6$ is F or F*.
8. The composition of claim 1, wherein $X^7$ is R or R*.
9. The composition of claim 1, wherein $X^8$ is S or S*.
10. The composition of claim 1, wherein:

$X^2$ is L or L*;
$X^3$ is P or P*;
$X^4$ is T or T*;
$X^5$ is K or K*;
$X^6$ is F or F*;
$X^7$ is R or R*; and
$X^8$ is S or S*.

11. The composition of claim 1, wherein Formula II is:

(SEQ ID NO: 11)

beta A—G—G—G—Cys-L—P—T—K—F—R—S—Cys.

12. A pharmaceutical composition comprising the composition of claim 1, and a pharmaceutically acceptable carrier.

\* \* \* \* \*

SEQUENCE LISTING

<160> NUMBER OF SEQ ID NOS: 26

<210> SEQ ID NO 1
<211> LENGTH: 9
<212> TYPE: PRT
<213> ORGANISM: Artificial Sequence
<220> FEATURE:
<223> OTHER INFORMATION: modified peptide for HER3 binding

<400> SEQUENCE: 1

Cys Leu Pro Thr Lys Phe Arg Ser Cys
1               5

<210> SEQ ID NO 2
<211> LENGTH: 4
<212> TYPE: PRT
<213> ORGANISM: Artificial Sequence
<220> FEATURE:
<223> OTHER INFORMATION: peptide linker
<220> FEATURE:
<221> NAME/KEY: VARIANT
<222> LOCATION: (1)..(1)
<223> OTHER INFORMATION: X can be bAla, 6-aminohexnoic acid,
      8-aminooctanoic acid or 2-(2-(2-aminoethoxy)ethoxy)acetic acid
<220> FEATURE:
<221> NAME/KEY: MOD_RES
<222> LOCATION: (1)..(1)
<223> OTHER INFORMATION: bAla
<220> FEATURE:
<221> NAME/KEY: MOD_RES
<222> LOCATION: (1)..(1)
<223> OTHER INFORMATION: 8-aminooctanoic acid
<220> FEATURE:
<221> NAME/KEY: MOD_RES
<222> LOCATION: (1)..(1)
<223> OTHER INFORMATION: 2-(2-(2-aminoethoxy)ethoxy)acetic acid
<220> FEATURE:
<221> NAME/KEY: MOD_RES
<222> LOCATION: (1)..(1)
<223> OTHER INFORMATION: 6-aminohexnoic acid
<220> FEATURE:
<221> NAME/KEY: VARIANT
<222> LOCATION: (2)..(2)
<223> OTHER INFORMATION: X can be natural or non-natural derivative of
      Gly, Ala, Ser, Pro, Trp, Tyr, His, Thr, Met, Asn, Gln
<220> FEATURE:
<221> NAME/KEY: VARIANT
<222> LOCATION: (3)..(3)
<223> OTHER INFORMATION: X can be natural or non-natural derivative of
      Gly, Ala, Ser, Pro, Trp, Tyr, His, Thr, Met, Asn, Gln
<220> FEATURE:
<221> NAME/KEY: VARIANT
<222> LOCATION: (4)..(4)
<223> OTHER INFORMATION: X can be natural or non-natural derivative of
      Gly, Ala, Ser, Pro, Trp, Tyr, His, Thr, Met, Asn, Gln

<400> SEQUENCE: 2

Xaa Xaa Xaa Xaa
1

<210> SEQ ID NO 3
<211> LENGTH: 4
<212> TYPE: PRT
<213> ORGANISM: Artificial Sequence
<220> FEATURE:
<223> OTHER INFORMATION: peptide linker
<220> FEATURE:
<221> NAME/KEY: MOD_RES
<222> LOCATION: (1)..(1)
<223> OTHER INFORMATION: bAla

<400> SEQUENCE: 3

Xaa Gly Gly Gly

```
<210> SEQ ID NO 4
<211> LENGTH: 13
<212> TYPE: PRT
<213> ORGANISM: Artificial Sequence
<220> FEATURE:
<223> OTHER INFORMATION: modified peptide for HER3 binding
<220> FEATURE:
<221> NAME/KEY: MOD_RES
<222> LOCATION: (1)..(1)
<223> OTHER INFORMATION: bAla
<220> FEATURE:
<221> NAME/KEY: DISULFID
<222> LOCATION: (5)..(13)
<223> OTHER INFORMATION: Disulfide bond
<220> FEATURE:
<221> NAME/KEY: VARIANT
<222> LOCATION: (6)..(12)
<223> OTHER INFORMATION: X can be any naturally occurring amino acid

<400> SEQUENCE: 4

Xaa Gly Gly Gly Cys Xaa Xaa Xaa Xaa Xaa Xaa Xaa Cys
1               5                   10

<210> SEQ ID NO 5
<211> LENGTH: 13
<212> TYPE: PRT
<213> ORGANISM: Artificial Sequence
<220> FEATURE:
<223> OTHER INFORMATION: modified peptide for HER3 binding
<220> FEATURE:
<221> NAME/KEY: MOD_RES
<222> LOCATION: (1)..(1)
<223> OTHER INFORMATION: bAla
<220> FEATURE:
<221> NAME/KEY: DISULFID
<222> LOCATION: (5)..(13)
<223> OTHER INFORMATION: Disulfide bond
<220> FEATURE:
<221> NAME/KEY: VARIANT
<222> LOCATION: (6)..(12)
<223> OTHER INFORMATION: X can be any naturally occurring amino acid

<400> SEQUENCE: 5

Xaa Gly Gly Gly Cys Xaa Xaa Xaa Xaa Xaa Xaa Xaa Cys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: modified peptide for HER3 binding
<220> FEATURE:
<221> NAME/KEY: MOD_RES
<222> LOCATION: (1)..(1)
<223> OTHER INFORMATION: bAla
<220> FEATURE:
<221> NAME/KEY: DISULFID
<222> LOCATION: (5)..(13)
<223> OTHER INFORMATION: Disulfide bond
<220> FEATURE:
<221> NAME/KEY: VARIANT
<222> LOCATION: (6)..(12)
<223> OTHER INFORMATION: X can be any naturally occurring amino acid

<400> SEQUENCE: 6

Xaa Gly Gly Gly Cys Xaa Xaa Xaa Xaa Xaa Xaa Xaa Cys
1               5                   10

<210> SEQ ID NO 7
```

```
<211> LENGTH: 13
<212> TYPE: PRT
<213> ORGANISM: Artificial Sequence
<220> FEATURE:
<223> OTHER INFORMATION: modified peptide for HER3 binding
<220> FEATURE:
<221> NAME/KEY: MOD_RES
<222> LOCATION: (1)..(1)
<223> OTHER INFORMATION: bAla
<220> FEATURE:
<221> NAME/KEY: DISULFID
<222> LOCATION: (5)..(13)
<223> OTHER INFORMATION: Disulfide bond

<400> SEQUENCE: 7

Xaa Gly Gly Gly Cys Leu Pro Thr Lys Phe Arg Ser Cys
1               5                   10

<210> SEQ ID NO 8
<211> LENGTH: 4
<212> TYPE: PRT
<213> ORGANISM: Artificial Sequence
<220> FEATURE:
<223> OTHER INFORMATION: terminal peptide modification to HER3 binding
      peptide
<220> FEATURE:
<221> NAME/KEY: VARIANT
<222> LOCATION: (1)..(1)
<223> OTHER INFORMATION: X can be bAla, 6-aminohexnoic acid,
      8-aminooctanoic acid or 2-(2-(2-aminoethoxy)ethoxy)acetic acid
<220> FEATURE:
<221> NAME/KEY: MOD_RES
<222> LOCATION: (1)..(1)
<223> OTHER INFORMATION: bAla
<220> FEATURE:
<221> NAME/KEY: MOD_RES
<222> LOCATION: (1)..(1)
<223> OTHER INFORMATION: 2-(2-(2-aminoethoxy)ethoxy)acetic acid
<220> FEATURE:
<221> NAME/KEY: MOD_RES
<222> LOCATION: (1)..(1)
<223> OTHER INFORMATION: 8-aminooctanoic acid
<220> FEATURE:
<221> NAME/KEY: MOD_RES
<222> LOCATION: (1)..(1)
<223> OTHER INFORMATION: 6-aminohexnoic acid
<220> FEATURE:
<221> NAME/KEY: VARIANT
<222> LOCATION: (2)..(2)
<223> OTHER INFORMATION: X can be natural or non-natural derivative of
      Gly, Ala, Ser, Pro, Trp, Tyr, His, Thr, Met, Asn, Gln
<220> FEATURE:
<221> NAME/KEY: VARIANT
<222> LOCATION: (3)..(3)
<223> OTHER INFORMATION: X can be natural or non-natural derivative of
      Gly, Ala, Ser, Pro, Trp, Tyr, His, Thr, Met, Asn, Gln
<220> FEATURE:
<221> NAME/KEY: VARIANT
<222> LOCATION: (4)..(4)
<223> OTHER INFORMATION: X can be natural or non-natural derivative of
      Gly, Ala, Ser, Pro, Trp, Tyr, His, Thr, Met, Asn, Gln

<400> SEQUENCE: 8

Xaa Xaa Xaa Xaa
1

<210> SEQ ID NO 9
<211> LENGTH: 4
<212> TYPE: PRT
<213> ORGANISM: Artificial Sequence
<220> FEATURE:
<223> OTHER INFORMATION: terminal peptide modification to HER3 binding
      peptide
<220> FEATURE:
<221> NAME/KEY: MOD_RES
```

```
<222> LOCATION: (1)..(1)
<223> OTHER INFORMATION: bAla

<400> SEQUENCE: 9

Xaa Gly Gly Gly
1

<210> SEQ ID NO 10
<211> LENGTH: 13
<212> TYPE: PRT
<213> ORGANISM: Artificial Sequence
<220> FEATURE:
<223> OTHER INFORMATION: modified peptide for HER3 binding
<220> FEATURE:
<221> NAME/KEY: MOD_RES
<222> LOCATION: (1)..(1)
<223> OTHER INFORMATION: bAla
<220> FEATURE:
<221> NAME/KEY: DISULFID
<222> LOCATION: (5)..(13)
<223> OTHER INFORMATION: Disulfide bond
<220> FEATURE:
<221> NAME/KEY: VARIANT
<222> LOCATION: (6)..(12)
<223> OTHER INFORMATION: X can be any naturally occurring amino acid

<400> SEQUENCE: 10

Xaa Gly Gly Gly Cys Xaa Xaa Xaa Xaa Xaa Xaa Xaa Cys
1               5                   10

<210> SEQ ID NO 11
<211> LENGTH: 13
<212> TYPE: PRT
<213> ORGANISM: Artificial Sequence
<220> FEATURE:
<223> OTHER INFORMATION: modified peptide for HER3 binding
<220> FEATURE:
<221> NAME/KEY: MOD_RES
<222> LOCATION: (1)..(1)
<223> OTHER INFORMATION: bAla
<220> FEATURE:
<221> NAME/KEY: DISULFID
<222> LOCATION: (5)..(13)
<223> OTHER INFORMATION: Disulfide bond

<400> SEQUENCE: 11

Xaa Gly Gly Gly Cys Leu Pro Thr Lys Phe Arg Ser Cys
1               5                   10

<210> SEQ ID NO 12
<211> LENGTH: 9
<212> TYPE: PRT
<213> ORGANISM: Artificial Sequence
<220> FEATURE:
<223> OTHER INFORMATION: modified peptide for HER3 binding
<220> FEATURE:
<221> NAME/KEY: DISULFID
<222> LOCATION: (1)..(9)
<223> OTHER INFORMATION: Disulfide bond
<220> FEATURE:
<221> NAME/KEY: VARIANT
<222> LOCATION: (2)..(2)
<223> OTHER INFORMATION: X can be natural or non-natural derivative of
      Leu, Ile, Pro, Val, Gly
<220> FEATURE:
<221> NAME/KEY: VARIANT
<222> LOCATION: (3)..(3)
<223> OTHER INFORMATION: X can be natural or non-natural derivative of
      Leu, Ile, Pro, Val, Gly
<220> FEATURE:
<221> NAME/KEY: VARIANT
<222> LOCATION: (4)..(4)
<223> OTHER INFORMATION: X can be natural or non-natural derivative of
```

```
        Thr, Ser, Cys, Met
<220> FEATURE:
<221> NAME/KEY: VARIANT
<222> LOCATION: (5)..(6)
<223> OTHER INFORMATION: X can be any natural or non-natural amino acid
<220> FEATURE:
<221> NAME/KEY: VARIANT
<222> LOCATION: (7)..(7)
<223> OTHER INFORMATION: X can be natural or non-natural derivative of
        Arg, His, Lys, Asn, Gln
<220> FEATURE:
<221> NAME/KEY: VARIANT
<222> LOCATION: (8)..(8)
<223> OTHER INFORMATION: X can be natural or non-natural derivative of
        Ser, Thr, Cys, Met

<400> SEQUENCE: 12

Cys Xaa Xaa Xaa Xaa Xaa Xaa Xaa Cys
1               5

<210> SEQ ID NO 13
<211> LENGTH: 9
<212> TYPE: PRT
<213> ORGANISM: Artificial Sequence
<220> FEATURE:
<223> OTHER INFORMATION: modified peptide for HER3 binding
<220> FEATURE:
<221> NAME/KEY: VARIANT
<222> LOCATION: (2)..(2)
<223> OTHER INFORMATION: X can be natural or non-natural derivative of
        Leu, Ile, Pro, Val, Gly
<220> FEATURE:
<221> NAME/KEY: VARIANT
<222> LOCATION: (3)..(3)
<223> OTHER INFORMATION: X can be natural or non-natural derivative of
        Leu, Ile, Pro, Val, Gly
<220> FEATURE:
<221> NAME/KEY: VARIANT
<222> LOCATION: (4)..(4)
<223> OTHER INFORMATION: X can be natural or non-natural derivative of
        Thr, Ser, Cys, Met
<220> FEATURE:
<221> NAME/KEY: VARIANT
<222> LOCATION: (5)..(6)
<223> OTHER INFORMATION: X can be any natural or non-natural amino acid
<220> FEATURE:
<221> NAME/KEY: VARIANT
<222> LOCATION: (7)..(7)
<223> OTHER INFORMATION: X can be natural or non-natural derivative of
        Arg, His, Lys, Asn, Gln
<220> FEATURE:
<221> NAME/KEY: VARIANT
<222> LOCATION: (8)..(8)
<223> OTHER INFORMATION: X can be natural or non-natural derivative of
        Ser, Thr, Cys, Met

<400> SEQUENCE: 13

Cys Xaa Xaa Xaa Xaa Xaa Xaa Xaa Cys
1               5

<210> SEQ ID NO 14
<211> LENGTH: 13
<212> TYPE: PRT
<213> ORGANISM: Artificial Sequence
<220> FEATURE:
<223> OTHER INFORMATION: modified peptide for HER3 binding
<220> FEATURE:
<221> NAME/KEY: MOD_RES
<222> LOCATION: (1)..(1)
<223> OTHER INFORMATION: bAla
<220> FEATURE:
<221> NAME/KEY: VARIANT
<222> LOCATION: (6)..(12)
<223> OTHER INFORMATION: X can be any naturally occurring amino acid
```

```
<400> SEQUENCE: 14

Xaa Gly Gly Gly Cys Xaa Xaa Xaa Xaa Xaa Xaa Xaa Cys
1               5                   10

<210> SEQ ID NO 15
<211> LENGTH: 13
<212> TYPE: PRT
<213> ORGANISM: Artificial Sequence
<220> FEATURE:
<223> OTHER INFORMATION: modified peptide for HER3 binding
<220> FEATURE:
<221> NAME/KEY: MOD_RES
<222> LOCATION: (1)..(1)
<223> OTHER INFORMATION: bAla
<220> FEATURE:
<221> NAME/KEY: VARIANT
<222> LOCATION: (6)..(12)
<223> OTHER INFORMATION: X can be any naturally occurring amino acid

<400> SEQUENCE: 15

Xaa Gly Gly Gly Cys Xaa Xaa Xaa Xaa Xaa Xaa Xaa Cys
1               5                   10

<210> SEQ ID NO 16
<211> LENGTH: 13
<212> TYPE: PRT
<213> ORGANISM: Artificial Sequence
<220> FEATURE:
<223> OTHER INFORMATION: 68Ga modified peptide for HER3 binding
<220> FEATURE:
<221> NAME/KEY: MOD_RES
<222> LOCATION: (1)..(1)
<223> OTHER INFORMATION: bAla
<220> FEATURE:
<221> NAME/KEY: VARIANT
<222> LOCATION: (6)..(12)
<223> OTHER INFORMATION: X can be any naturally occurring amino acid

<400> SEQUENCE: 16

Xaa Gly Gly Gly Cys Xaa Xaa Xaa Xaa Xaa Xaa Xaa Cys
1               5                   10

<210> SEQ ID NO 17
<211> LENGTH: 13
<212> TYPE: PRT
<213> ORGANISM: Artificial Sequence
<220> FEATURE:
<223> OTHER INFORMATION: 68Ga modified peptide for HER3 binding
<220> FEATURE:
<221> NAME/KEY: MOD_RES
<222> LOCATION: (1)..(1)
<223> OTHER INFORMATION: bAla

<400> SEQUENCE: 17

Xaa Gly Gly Gly Cys Leu Pro Thr Lys Phe Arg Ser Cys
1               5                   10

<210> SEQ ID NO 18
<211> LENGTH: 13
<212> TYPE: PRT
<213> ORGANISM: Artificial Sequence
<220> FEATURE:
<223> OTHER INFORMATION: modified peptide for HER3 binding
<220> FEATURE:
<221> NAME/KEY: MOD_RES
<222> LOCATION: (1)..(1)
<223> OTHER INFORMATION: bAla

<400> SEQUENCE: 18

Xaa Gly Gly Gly Cys Leu Pro Thr Lys Phe Arg Ser Cys
```

```
1               5                  10
```

<210> SEQ ID NO 19
<211> LENGTH: 9
<212> TYPE: PRT
<213> ORGANISM: Artificial Sequence
<220> FEATURE:
<223> OTHER INFORMATION: modified peptide for HER3 binding
<220> FEATURE:
<221> NAME/KEY: VARIANT
<222> LOCATION: (2)..(8)
<223> OTHER INFORMATION: X can be any naturally occurring amino acid

<400> SEQUENCE: 19

```
Cys Xaa Xaa Xaa Xaa Xaa Xaa Xaa Cys
1               5
```

<210> SEQ ID NO 20
<211> LENGTH: 9
<212> TYPE: PRT
<213> ORGANISM: Artificial Sequence
<220> FEATURE:
<223> OTHER INFORMATION: peptide that binds HER3
<220> FEATURE:
<221> NAME/KEY: DISULFID
<222> LOCATION: (1)..(9)
<223> OTHER INFORMATION: Disulfide bond
<220> FEATURE:
<221> NAME/KEY: VARIANT
<222> LOCATION: (2)..(2)
<223> OTHER INFORMATION: X can be natural or non-natural derivative of
      Leu
<220> FEATURE:
<221> NAME/KEY: VARIANT
<222> LOCATION: (3)..(3)
<223> OTHER INFORMATION: X can be natural or non-natural derivative of
      Pro
<220> FEATURE:
<221> NAME/KEY: VARIANT
<222> LOCATION: (4)..(4)
<223> OTHER INFORMATION: X can be natural or non-natural derivative of
      Thr
<220> FEATURE:
<221> NAME/KEY: VARIANT
<222> LOCATION: (5)..(5)
<223> OTHER INFORMATION: X can be natural or non-natural derivative of
      Lys
<220> FEATURE:
<221> NAME/KEY: VARIANT
<222> LOCATION: (6)..(6)
<223> OTHER INFORMATION: X can be natural or non-natural derivative of
      Phe
<220> FEATURE:
<221> NAME/KEY: VARIANT
<222> LOCATION: (7)..(7)
<223> OTHER INFORMATION: X can be natural or non-natural derivative of
      Arg
<220> FEATURE:
<221> NAME/KEY: VARIANT
<222> LOCATION: (8)..(8)
<223> OTHER INFORMATION: X can be natural or non-natural derivative of
      Ser

<400> SEQUENCE: 20

```
Cys Xaa Xaa Xaa Xaa Xaa Xaa Xaa Cys
1               5
```

<210> SEQ ID NO 21
<211> LENGTH: 9
<212> TYPE: PRT
<213> ORGANISM: Artificial Sequence
<220> FEATURE:
<223> OTHER INFORMATION: modified peptide for HER3 binding

```
<400> SEQUENCE: 21

Cys Leu Pro Thr Lys Phe Arg Ser Cys
1               5

<210> SEQ ID NO 22
<211> LENGTH: 9
<212> TYPE: PRT
<213> ORGANISM: Unknown
<220> FEATURE:
<223> OTHER INFORMATION: peptide that binds HER3
<220> FEATURE:
<221> NAME/KEY: DISULFID
<222> LOCATION: (1)..(9)
<223> OTHER INFORMATION: Disulfide bond

<400> SEQUENCE: 22

Cys Leu Pro Thr Lys Phe Arg Ser Cys
1               5

<210> SEQ ID NO 23
<211> LENGTH: 9
<212> TYPE: PRT
<213> ORGANISM: Unknown
<220> FEATURE:
<223> OTHER INFORMATION: peptide that does not demonstrate HER3 specific
      binding

<400> SEQUENCE: 23

Cys His Glu Gln Gln Asn Pro His Cys
1               5

<210> SEQ ID NO 24
<211> LENGTH: 9
<212> TYPE: PRT
<213> ORGANISM: Unknown
<220> FEATURE:
<223> OTHER INFORMATION: peptide that does not demonstrate HER3 specific
      binding

<400> SEQUENCE: 24

Cys His Lys His Lys Asp Ser Gln Cys
1               5

<210> SEQ ID NO 25
<211> LENGTH: 9
<212> TYPE: PRT
<213> ORGANISM: Unknown
<220> FEATURE:
<223> OTHER INFORMATION: peptide that does not demonstrate HER3 specific
      binding

<400> SEQUENCE: 25

Cys His Leu Gly Glu Met Gly His Cys
1               5

<210> SEQ ID NO 26
<211> LENGTH: 4
<212> TYPE: PRT
<213> ORGANISM: Artificial Sequence
<220> FEATURE:
<223> OTHER INFORMATION: terminal peptide modification to HER3 binding
      peptide
<220> FEATURE:
<221> NAME/KEY: VARIANT
<222> LOCATION: (1)..(1)
<223> OTHER INFORMATION: X can be replaced by bAla
<220> FEATURE:
<221> NAME/KEY: MOD_RES
<222> LOCATION: (1)..(1)
```

```
<223> OTHER INFORMATION: bAla
<220> FEATURE:
<221> NAME/KEY: VARIANT
<222> LOCATION: (2)..(2)
<223> OTHER INFORMATION: X can be natural or non-natural derivative of
      Gly
<220> FEATURE:
<221> NAME/KEY: VARIANT
<222> LOCATION: (3)..(3)
<223> OTHER INFORMATION: X can be natural or non-natural derivative of
      Gly
<220> FEATURE:
<221> NAME/KEY: VARIANT
<222> LOCATION: (4)..(4)
<223> OTHER INFORMATION: X can be natural or non-natural derivative of
      Gly

<400> SEQUENCE: 26

Xaa Xaa Xaa Xaa
 1
```